(12) United States Patent
Thorpe et al.

(10) Patent No.: US 12,372,439 B2
(45) Date of Patent: Jul. 29, 2025

(54) APPARATUSES, SYSTEMS, AND METHODS FOR DETERMINING GAS EMISSION RATE DETECTION SENSITIVITY AND GAS FLOW SPEED USING REMOTE GAS CONCENTRATION MEASUREMENTS

(71) Applicant: Bridger Photonics, Inc., Bozeman, MT (US)

(72) Inventors: Michael James Thorpe, Bozeman, MT (US); Aaron Thomas Kreitinger, Bozeman, MT (US)

(73) Assignee: Bridger Photonics, Inc., Bozeman, MT (US)

( * ) Notice: Subject to any disclaimer, the term of this patent is extended or adjusted under 35 U.S.C. 154(b) by 250 days.

(21) Appl. No.: 18/054,517

(22) Filed: Nov. 10, 2022

(65) Prior Publication Data

US 2023/0221219 A1 Jul. 13, 2023

Related U.S. Application Data

(60) Provisional application No. 63/298,134, filed on Jan. 10, 2022.

(51) Int. Cl.
*G01N 1/22* (2006.01)
*G01N 15/06* (2024.01)
(Continued)

(52) U.S. Cl.
CPC ....... *G01N 1/2247* (2013.01); *G01N 15/0612* (2013.01); *G01N 21/8851* (2013.01);
(Continued)

(58) Field of Classification Search
CPC .... G01N 1/2247; G01N 15/06; G01N 15/075; G01N 15/0612; G01N 21/3504;
(Continued)

(56) References Cited

U.S. PATENT DOCUMENTS 6,087,977 A 7/2000 Rost
8,010,300 B1 * 8/2011 Stearns ................... G01S 17/95
356/326

(Continued)

FOREIGN PATENT DOCUMENTS

EP 2909598 B1 * 7/2018 .............. G01M 3/20
KR 102070288 B1 * 1/2021
(Continued)

OTHER PUBLICATIONS

International Search Report and Written Opinion for International Patent Application No. PCT/US2022/079669 dated Mar. 16, 2023, pp. all.
History+, meteoblue, https://www.meteoblue.com/en/historyplus, accessed Feb. 3, 2023.
Land-Based Station, National Centers for Environmental Information—National Oceanic and Atmospheric Administration, https://www.ncei.noaa.gov/products/land-based-station, accessed Feb. 3, 2023.
Lumen, Baker Hughes Company, https://www.bakerhughesds.com/measurement-sensing/lumen (2022), accessed Feb. 3, 2023.
(Continued)

*Primary Examiner* — Peter J Macchiarolo
*Assistant Examiner* — Monica S Young
(74) *Attorney, Agent, or Firm* — Dorsey & Whitney LLP

(57) ABSTRACT

Apparatuses systems and methods for gas emission rate detection sensitivity and probability of detection (PoD) based on emission rate. A measurement system may be characterized by its ability to detect gas plumes as a function of the emission rate of those plumes. The measurement system may be characterized based on a generalized PoD function which expresses PoD relative to emission rate as a function of gas concentration noise and gas flow speed. In an example application, the PoD may be used to estimate a cumulative distribution of gas plumes which were not detected based on a cumulative distribution of measured gas plumes. In another example application, the PoD may be used to refine an estimate for a measured emission rate.

25 Claims, 16 Drawing Sheets

(51) Int. Cl.
*G01N 15/075* (2024.01)
*G01N 21/3504* (2014.01)
*G01N 21/88* (2006.01)
*G01N 33/00* (2006.01)

(52) U.S. Cl.
CPC ........... *G01N 15/06* (2013.01); *G01N 15/075* (2024.01); *G01N 21/3504* (2013.01); *G01N 2021/8887* (2013.01); *G01N 33/0004* (2013.01)

(58) Field of Classification Search
CPC ........... G01N 21/8851; G01N 33/0004; G01N 2015/0046; G01N 2021/1793; G01N 2021/3531; G01N 2021/8887
USPC .......................................................... 73/23.2
See application file for complete search history.

(56) References Cited

U.S. PATENT DOCUMENTS

| | | | |
|---|---|---|---|
| 8,732,524 B2 | 5/2014 | Barton et al. | |
| 9,599,529 B1* | 3/2017 | Steele | G01N 33/0075 |
| 9,970,756 B2 | 5/2018 | Kreitinger et al. | |
| 2003/0065273 A1 | 4/2003 | Mault et al. | |
| 2006/0262311 A1* | 11/2006 | Muta | G01N 21/31 |
| | | | 356/437 |
| 2010/0131207 A1* | 5/2010 | Lippert | G01S 17/95 |
| | | | 702/49 |
| 2017/0097274 A1* | 4/2017 | Thorpe | G01C 15/00 |
| 2017/0176182 A1* | 6/2017 | Rella | G01M 3/22 |
| 2019/0376890 A1* | 12/2019 | Bennett | G06T 7/73 |
| 2020/0149883 A1* | 5/2020 | Thorpe | G01P 5/00 |
| 2020/0355552 A1* | 11/2020 | Kreitinger | G01M 3/38 |
| 2021/0140934 A1* | 5/2021 | Smith | G06V 20/17 |
| 2023/0176023 A1* | 6/2023 | Wang | G01N 33/0034 |
| | | | 340/632 |

FOREIGN PATENT DOCUMENTS

| | | | | |
|---|---|---|---|---|
| WO | 2019099567 | | 5/2019 | |
| WO | WO-2019099567 A1 * | | 5/2019 | G01J 3/4338 |
| WO | WO-2019152787 A1 * | | 8/2019 | G01M 3/16 |
| WO | WO-2020150388 A1 * | | 7/2020 | B64C 39/024 |
| WO | 2023132998 A1 | | 7/2023 | |

OTHER PUBLICATIONS

Methane Performance Specifications, Boreal Laser, https://boreal-laser.com/gases/methane/, accessed Feb. 3, 2023.
Soofie, Scientific Aviation, https://www.scientificaviation.com/soofie/ (2022), accessed Feb. 3, 2023.
The High-Resolution Rapid Refresh (HRRR), Global Systems Laboratory, NOAA Research, National Oceanic & Atmospheric Administration, U.S. Department of Commerce, https://rapidrefresh.noaa.gov/hrrr/ (2020), accessed Feb. 3, 2023.
Thermal imaging provides early leak detection in oil and gas pipelines, Teledyne FLIR, https://www.flir.com/discover/Instruments/condition-monitoring/intelliview-for-oil-and-gas/, 2021, accessed Feb. 3, 2023.
Alden, C B, et al., Single-Blind Quantification of Natural Gas Leaks from 1 km Distance Using Frequency Combs, Environmental Science & Technology, vol. 53, pp. 2908-2917, (2019).
Iseki, T , et al., A portable remote methane sensor using tunable diode laser, Measurement Science and Technology, vol. 11, pp. 594-602, (2000).
Johnson, M R, et al., 'Blinded evaluation of airborne methane source detection using Bridger Photonics LiDAR,' Remote Sensing of Environment, vol. 259, 112418, (2021).
Johnson, M R, et al., Where the Methane Is—Insights from Novel Airborne LiDAR Measurements Combined with Ground Survey Data, Environmental Science & Technology, vol. 55, pp. 9773-9783, (2021).
Sandsten, J , et al., Volume flow calculations on gas leaks imaged with infrared gas-correlation, Optics Express, vol. 20, p. 20318-20329 (2012).
Sherwin, E D, et al., Single-blind test of airplane-based hyperspectral methane detection via controlled releases, Elem Sci Anth, art 9(1), (2021).
Thorpe, A K, et al., Mapping methane concentrations from a controlled release experiment using the next generation airborne visible/infrared imaging spectrometer (AVIRIS-NG), Remote Sensing of Environment, vol. 179, pp. 104-115, (2016).
Examination Report for AU Patent App. 2022431237, mailed on Mar. 20, 2025, pp. all.
Office Action for Canadian Patent Application No. 3,241,188, dated Apr. 30, 2025, pp. all.

* cited by examiner

APPARATUSES, SYSTEMS, AND METHODS FOR DETERMINING GAS EMISSION RATE DETECTION SENSITIVITY AND GAS FLOW SPEED USING REMOTE GAS CONCENTRATION MEASUREMENTS

CROSS-REFERENCE TO RELATED APPLICATION(S)

This application claims the benefit under 35 U.S.C. § 119 of the earlier filing date of U.S. Provisional Application Ser. No. 63/298,134 filed Jan. 10, 2022, the entire contents of which are hereby incorporated by reference in their entirety for any purpose.

STATEMENT REGARDING RESEARCH & DEVELOPMENT

This invention was made with government support under DE-AR0001389 awarded by the Department of Energy. The government has certain rights in the invention.

TECHNICAL FIELD

Examples described herein relate generally to the fields of remote sensing of gases, gas sensing lidar, laser spectroscopy, airborne lidar detection and imaging of gas plumes, gas emission rate quantification, gas flow speed estimation, gas concentration detection sensitivity estimation, and emission rate detection sensitivity estimation. Examples in the field of airborne lidar emission detection, localization, and quantification are described.

BACKGROUND

Sensors for monitoring gas concentrations and quantifying gas emission rates can be important tools for a wide variety of traditional and emerging applications including: detection and quantification of emissions from waste (e.g. landfills or wastewater processing facilities) and industrial (e.g. oil and gas) and agricultural (e.g. feedlot and farmland) infrastructures; quantifying and tracking sources and sinks of air pollution; monitoring atmospheric composition; and understanding atmospheric chemistry.

Many sensor technologies have been developed and deployed for gas concentration mapping and monitoring. Examples include active remote gas sensing techniques, such as light detection and ranging (lidar) and open path spectroscopy systems, as well as passive remote sensing techniques including solar infrared imaging spectrometers (e.g. solar infrared spectrometers), and optical gas imaging (e.g. thermal infrared) cameras. In addition to remote sensing techniques, point sensors in distributed networks or on mobile platforms can be deployed to enable gas concentration measurements at discrete locations.

An important measured quantity may be a gas concentration, which may refer to the amount of a gas (e.g. density, volume, mass, fractional, etc.) at a given location(s) in space. A gas concentration level (e.g. measured by a point sensor) may be a direct indicator of safety (e.g. the lower explosive limit of methane is 50,000 ppm) at a specific point in space. Remote sensors may measure a path-integrated gas concentration, which may refer to an amount of gas (e.g. summed, integrated, etc.) present along a path or column of gas. A path-averaged gas concentration may refer to the average amount of gas along a path or column of gas. Knowledge of the gas plume spatial extent along the path or column (e.g. through remote measurements from multiple perspectives/angles), may enable matching of a gas concentration vertical profile with a wind speed vertical profile. Other forms or representations of gas concentration may also exist.

A gas emission rate may differ from a gas concentration in that a gas emission rate may refer to an amount (e.g. mass, volume, etc.) of gas emitted from an orifice or geographic area, or passing through a surface (e.g. an imaginary plane), over a given time (e.g. per unit time). Gas emission rate may sometimes be referred to as leak rate, flux, or other terms. Gas emission rate may be an important indicator for example to enable emissions reduction, gas certification, emissions accounting, emissions inventories, sustainability initiatives, or combinations thereof.

Approaches for measuring emission rate may include combining gas flow speed (e.g. wind data) with gas concentration spatial mapping data from one or more remote gas imaging technologies to perform a computation that produces an emission rate estimate. Several performance tradeoffs exist between the various types of sensors for gas concentration mapping. Remote gas mapping techniques may perform better for localizing gas sources due to their ability to rapidly visualize an entire plume, including the emission source. Plume visualization may enable real-time or rapid localization of an emission source once a region of elevated gas has been detected, and may significantly improve the ability to accurately estimate emission rate.

Performance tradeoffs also exist between the various methods for performing emission rate measurements—both for the gas concentration mapping and gas flow speed (e.g. sometimes determined by wind speed) estimation techniques that may be employed. For instance, passive remote sensors may enable fast acquisition of plume image frames allowing the application of velocity detection algorithms, such as block matching, to determine emission rate. Also, the tracer correlation method for measuring emission rate may rely on highly sensitive, selective and accurate mobile point sensor concentration measurements, but also on controlled releases of a tracer gas from the location under test, making it cumbersome and costly to implement. A more common point sensor approach to measuring emission rate over larger areas, often referred to as a mass balance measurement, involves mobile concentration measurements that follow approximately closed-path trajectories around an area under test. While the tracer correlation method and mass balance measurement may produce reliable results, they also require long measurement durations—mainly due to the large number of closed-path passes required to produce an accurate emission rate estimate and rely on relatively stable emission rates and wind conditions throughout the measurement duration. Furthermore, these methods may produce low spatial resolution information regarding the location of the emission source due to the large spatial extent of the closed-path trajectories.

Lidar techniques such as differential absorption lidar (DIAL) and tunable diode laser absorption spectroscopy (TDLAS) lidar, when paired with beam-scanning technology and navigation data, combine the desirable attributes of high-precision laser-based gas concentration measurements and the rapid spatial coverage of gas imaging cameras. Lidar can achieve high spectral selectivity of targeted gas species and insensitivity to ambient light conditions through laser illumination of remote targets and highly selective detection schemes applied to received light. Laser illumination of the measurement scene minimizes systematic noise on remote gas concentration measurements and enables accurate estimation of the noise associated with each remote gas concentration measurement. Additionally, recent innovation in gas sensing lidar systems have demonstrated sufficient measurements rates to enable the generation of gas plumes imagery. These properties of lidar sensors may make them well suited for reliable detection and quantification of regions of anomalous gas concentration, which may be used to find and prioritize emissions. Lidar gas concentration measurements may also be used to produce accurate emission rate estimates by combining gas concentration measurement with gas flow speed information.

Obtaining gas flow speed estimates corresponding to the gas plume location may be useful for the determination of an emission rate. In some instances, wind speed may be used to estimate gas flow speed. The use of wind speed herein does not preclude the use of other gas flow speed determination methods. An approach used to acquire wind data in the vicinity of emission sources may include positioning one or several anemometer(s), at known height(s) above ground, near the measurement locations. This approach has been shown to produce reliable and accurate wind speed and direction information that may be used to produce accurate emission rate estimates. However, in cases where large geographic areas are being measured, especially from a mobile platform, such as an aircraft, placing anemometers near all measurement locations may be impractical. Another option for estimating wind speed and direction data may be to access (and possibly interpolate) observations recorded at nearby weather stations. This data may be available for download from a number of online services such as the National Climatic Data Center operated by NOAA, MesoWest operated by the University of Utah and Weather Underground. Weather station wind speed and direction data is typically recorded at a height of 10 m above ground level, and may provide reliable wind speed and direction information in cases where emission rate estimates are performed near an automatically archived weather station. Finally, weather modeling services such as Meteoblue and NOAA NAM and HRRR use weather station observations and topography data as inputs to high spatial resolution weather models to estimate or interpolate wind speed and direction data at locations other than the locations of the weather stations, effectively filling in the gaps between weather station locations.

Reliable and/or accurate determination of an emission rate detection sensitivity may be important to assess the effectiveness of a given emissions reduction strategy. For instance, confident detection (and remediation) of methane emissions greater than 3 kg/hr may result in a >90% reduction in methane emissions across a typical oil and gas production basin. Also, confident emission rate detection sensitivity of 3 kg/hr may be necessary to effectively quantify the aggregate emissions inventory across the asset portfolio of an oil and gas owner or operator. Given the importance of the emission rate detection sensitivity, a regulatory body, an owner or operator of oil and gas infrastructure, or other interested party, may therefore desire or demand that an emission rate detection sensitivity be reliably and accurately known for a given site/spatial region or across multiple sites/spatial regions of interest.

However, significant challenges exist to reliably and accurately determining an emission rate detection sensitivity, largely because (a) the emission rate detection sensitivity may depend on operational and environmental factors and (b) detecting emissions may be statistical and probabilistic in nature. Operational parameters may be more or less under the control of a sensor operator. For instance, for an airborne remote sensor (e.g. lidar), the flight altitude, flight speed, point density, illuminating optical power, measurement pixel size, and sensor field of view may be operational parameters that affect the emission rate detection sensitivity, but are more or less controlled during a measurement. Conversely, other (e.g. environmental) parameters that may affect the emission rate detection sensitivity, such as gas flow speed, ground surface reflectivity, sunlight conditions, and local topography, may not be well controlled or readily known during a measurement. The fact that the emission rate detection sensitivity performance of a remote sensor depends on so many environmental and operational parameters and may be probabilistic and/or statistical in nature makes determining and implementing an "envelope" of conditions necessary to achieve a given emission rate detection sensitivity performance exceedingly challenging. This many-dimensional and statistical parameter space may be impractical to adequately characterize, so the performance of a remote sensor under large portions of the parameter space may be unknown or unverified. Moreover, with regard to gas flow speed, even if an estimate of gas flow speed (e.g. wind speed) is known, the estimate may be inaccurate, which may result in an inaccurate estimate of the emission rate and the emission rate detection sensitivity. The invention disclosed herein solves the problem of determining an emission rate detection sensitivity performance when a multi-dimensional and/or statistical parameter space may be complex, intractable, incomplete, or inaccurate.

SUMMARY

In at least one aspect, the present disclosure relates to a method which includes collecting a plurality of gas concentration measurements of gas plumes with known emission rates with a remote gas sensor, determining true positive anomalous gas concentration detections from the plumes with known emission rates, determining a gas concentration noise associated with one or more of the plurality of gas concentration measurements, determining a gas flow speed corresponding to one or more of the plumes with known emission rates, generating one or more probability of detection (PoD) functions over an interval of gas concentration noise and gas flow speed based on the plumes with the known emission rates, and constructing a generalized PoD function associated with the measurement system using the one or more PoD functions.

The method may include determining the one or more PoD functions based on a sensitivity function. The method may include spatially resampling the gas concentration measurements and using the spatially resampled gas concentration measurements to generate the one or more PoD functions. The spatial resampling may be to a uniform grid pattern.

The method may include constructing the generalized PoD function based on a model that characterizes the emission rate PoD of the measurement system as a function of gas flow speed and gas concentration noise. The method may include generating the one or more PoD functions based on fitting data points from a gas sensitivity function or a logistic regression of the gas concentration measurements.

The method may include collecting a plurality of field gas concentration measurements corresponding to emissions with unknown emission rates, determining emission rates based on the plurality of field gas concentration measurements, and using the generalized PoD function and environmental conditions corresponding to the measurement collection to estimate a number and associated rates of false negative emission sources based on emission rates determined from detected emissions.

The method may include determining the gas concentration noise based on a noise model. The method may include collecting the plurality of gas concentration measurements with a lidar system. The method may include characterizing a detection sensitivity performance of the measurement system based on the generalized PoD function.

In at least one aspect, the present disclosure relates to a system which includes a remote senor, a processor, and a memory. The remote sensor collects sensor measurements of a gas plume. The memory includes non-transitory instructions which, when executed by the processor cause the processor to determine a gas concentration measurement based on the measurement collected by the remote sensor and a gas concentration noise level associated with the gas concentration measurement, determine a gas flow speed associated with the gas plume, determine an emission rate based on the gas concentration measurement and gas flow speed information, and combine a generalized probability of detection (PoD) function associated with the lidar system with the gas flow speed and the gas concentration noise to determine a detection sensitivity performance.

The remote sensor may be mounted on a mobile platform. The remote sensor may include a beam scanner configured to scan a laser across an environment. The remote sensor may include a receiver configured to record the measurements based on light received as the laser is scanned across the environment.

The non-transitory instructions when executed by the processor may further cause the computing system to determine a detection sensitivity performance based on the generalized PoD function. The non-transitory instructions when executed by the processor may further causes the computing system to adjust the emission rate based, in part, on the generalized PoD function and a second PoD based on the gas concentration noise.

In at least one aspect, the present disclosure relates to a method which includes determining measured emission rates of gas plumes based on gas flow speed information and gas concentration measurements collected with a measurement system, generating a cumulative distribution of the gas plumes based on the determined emission rates, and determining a number of emission sources or amount of emissions attributed to false negative detections based the generalized probability of detection (PoD) function of the measurement system.

The method may include generating the generalized PoD function based on measurements of a known emission source with the measurement system. The method may include generating an adjusted cumulative distribution relative to the estimated cumulative distribution. The method may include displaying the cumulative distribution, the estimated distribution, the adjusted cumulative distribution or combinations thereof.

In at least one aspect, the present disclosure relates to a method which includes detecting a gas plume based on a gas concentration measurement, determining a first probability of detection (PoD) value based on the gas concentration measurement, combining the gas concentration measurement with a gas flow speed to determine an initial emission rate of the gas plume, determining a second PoD value based on the gas concentration measurement and the gas flow speed and a generalized PoD function, and finding an adjusted emission rate of the gas plume based on the initial emission rate, the first PoD value and the second PoD value.

The method may include finding the adjusted emission rate based on finding an estimated emission rate where the first PoD value matches the second PoD value. The method may include determining the adjusted emission rate based on a weighted average of the initial emission rate and the estimated emission rate. The method may include determining the first probability of detection based on a gas concentration noise based on the gas concentration measurement. The method may include determining the generalized PoD function based on measurements of a known emission rate.

DETAILED DESCRIPTION

Figure 1:
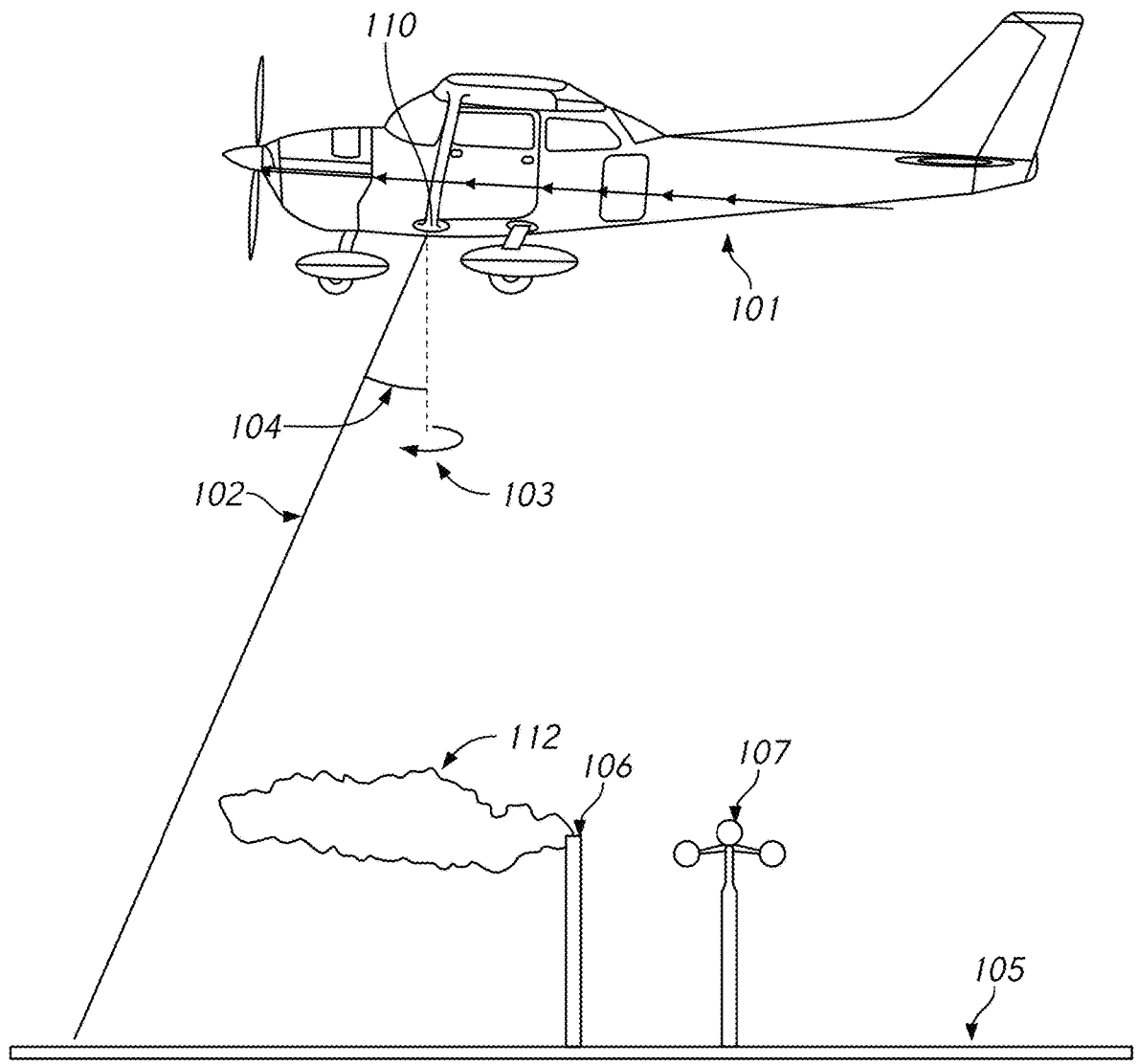
FIG. 1 is an example measurement setup for remote gas plume detection, localization, and quantification of controlled emission rate gas plumes.

The following description of certain embodiments is merely exemplary in nature and is in no way intended to limit the scope of the disclosure or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the disclosure. Moreover, for the purpose of clarity, detailed descriptions of certain features will not be discussed when they would be apparent to those with skill in the art so as not to obscure the description of embodiments of the disclosure. The following detailed description is therefore not to be taken in a limiting sense, and the scope of the disclosure is defined only by the appended claims. For example, while methane gas may be used in certain context herein, the method may apply to any gas species.

A variety of applications may include identifying and/or quantifying gas plumes or emissions within an environment. For example, detecting leaks in an industrial site such as an oil or gas production facility, a landfill, a storage facility etc. Gas concentration measurements may be used to measure a concentration of one or more gases of interest (e.g., methane, CO2, etc). For example, a detection system (e.g. lidar, solar infrared spectrometry, etc.) may scan an area and collect gas concentration measurements (e.g. path-integrated gas concentration measurements). The gas concentration measurements may be combined with a measurement and/or estimate of gas flow speed (e.g., a wind speed measurement) to generate measurements of emission rate.

However, while the measurement alone may provide useful information, it may also be useful to determine a confidence in the measurement, or the likelihood that emission events were not detected (e.g. false negatives). For example, it may be useful to determine a probability that a gas plume or emission source will be detected as a function of the emission rate of that plume. For example, because the environmental and operational parameters may change from one site to another, it may be desirable to determine a probability of detecting a leak with a given emission rate, or to determine an emission rate that can be detected given a probability of detection, for each individual site or piece of equipment, or group thereof. Such information may, for instance, be valuable to ensure that a certain detection sensitivity performance is achieved in measuring the sites or equipment (e.g. to meet regulatory compliance). The detection sensitivity performance may represent an emission rate, a PoD, the emission rate for which a certain PoD is achieved, a PoD for a given emission rate, or combinations thereof. A relatively large number of different parameters may affect the performance of the measurement system. Thus, there may be a need to characterize the performance of the measurement system in a manner which requires relatively few independent variables.

The present disclosure is drawn to apparatuses, systems, and methods for determining gas emission rate sensitivity and gas flow speed using remote gas concentration measurements. A measurement system may be characterized by a generalized probability of detection (PoD) function. The generalized PoD function may represent a model which expresses the PoD at different emission rates based on gas flow speed and gas concentration noise. The gas flow speed may be a property which is determined as part of determining the emission rate. The gas concentration noise may combine a plurality of measurement parameters (e.g., received optical power, measurement point density, altitude, flight speed, ground reflectivity, etc) into a parameter of lower dimensionality which may be determined based on measured properties of the signal, or noise, such as SNR. Once a generalized PoD function is developed for a measurement system, measurements of the gas flow speed and/or gas concentration noise may be used to further characterize a performance of the system (e.g., to determine a confidence in a measurement, a lower limit of detection for given measurement conditions, a probability of detection, etc.). Since the generalized PoD function relies on two parameters (gas flow speed and gas concentration noise) which may be readily determined, it may be a relatively powerful tool for characterizing a measurement system.

Embodiments of the disclosure may include generating a generalized PoD function for a measurement system. As part of this process gas concentration measurements may be collected of one or more gas plumes with known emission rates (e.g., from a metered emission source). The measurements may be classified based on whether or not each measurement detected the gas plume or not, as well as a gas concentration noise and measured gas flow speed associated with that measurement. Based on the data set, one or more PoD functions based on gas concentration noise, gas flow speed or combinations thereof relative to the known emission rates may be determined. Based on these one or more PoD functions, a generalized PoD function may be constructed. In some embodiments, a model (e.g. based on physical understanding of the sensor and parameters) may replace, or be informed by, or be validated by, the use of measurements of emissions with known emission rates to generate the generalized PoD function.

Embodiments of the present disclosure also describe example applications which may use the generalized PoD function. For example, the generalized PoD function may be used to generate a corrected set of data which estimates characteristics (e.g. number or emission rates) of emission events or sites which were not directly measured, but still may exist. For example, a site may be measured and different emissions, each with an emission rate, may be detected (e.g., based on gas concentration and flow speed measurements) and a cumulative distribution based on emission rate determined. Based on gas concentration noise and flow speed measurements, the generalized PoD function may be used to determine a PoD for one or more detected emission sources. The PoDs for the one or more detected emission sources may be used to determine an estimated cumulative distribution of different gas emissions, which may include an estimate of emission sources that were not detected. This is just one example, and alternative calculations may also be used to estimate undetected emissions based on known detection performance.

In another example application, the generalized PoD function may be used to determine an adjusted gas flow speed to obtain an updated emission rate. Gas flow speed information at the plume location, whether from measurement or model, may generally be more prone to greater error than measurements of concentration. Gas concentration noise may be used on its own to generate a PoD (e.g., $PoD_{GC}$). This may be compared to a measurement of the PoD based on the emission rate (e.g., $PoD_{ER}$) from the generalized PoD function. Since $PoD_{ER}$ depends on gas flow speed (as well as gas concentration noise) and $PoD_{GC}$ does not, if there is a mismatch, it may be assumed to be a problem in the gas flow speed information. Accordingly, based on the $PoD_{GC}$ and $PoD_{ER}$ the measured emission rate may be adjusted (e.g., by adjusting the estimated gas flow speed).

FIG. 1 is an example measurement setup for remote gas plume detection, localization, and quantification of controlled emission rate gas plumes. The measurement setup includes a lidar system 110 which is mounted on a mobile platform 101. In the example of FIG. 1, the mobile platform 101 is represented as a manned aircraft, however other types of mobile platforms such as unmanned aircrafts (e.g., drones) may also be used. In some embodiments, the lidar system 110 may be stationary (e.g., affixed to a mast or building). The lidar system 110 emits a transmitted laser beam 102 which may be scanned about the scene. The laser beam 102 interacts with the environment and returned light is received by the lidar system 110. Based on the returned light, the lidar system may determine a gas concentration (e.g. path-integrated gas concentration) measurement. Based on motion of the laser beam scanning 102 and/or a mobile platform 101, or combination thereof, the beam 102 may be scanned across the terrain 105. Multiple measurements may be collected to build up a number of gas concentration measurements across different points of the terrain 105, and potentially measured from different perspectives (e.g. viewing locations and angles).

While the present disclosure is generally described with respect to a lidar based gas concentration detection system, it is understood that the lidar sensor could represent any general gas concentration remote sensor (e.g. solar or thermal infrared spectrometer). Moreover, it is understood that some gas concentration remote sensors do not utilize scanning and instead image terrain or a scene onto an array of detectors. In general, whether by scanning a sensor's laser beam or field of view, or by the sensor imaging terrain or scene onto a detector array, an image of spatial gas concentrations across a scene may be generated.

For example, the lidar system 110 may scan the laser beam 102 in a conical pattern around the nadir direction 103 at an angle 104 that defines the field of view of the lidar system 110. The conical scan pattern is translated over the terrain 105 by the aircraft motion to create a lidar scan area.

The lidar scan area may include one or more regions of anomalous gas concentration 112. The region of anomalous gas concentration 112 may be generally referred to as a gas plume. The gas plume 112 may represent an area where one or more target gases are at a higher concentration than would normally be expected. In other words, the gas plume 112 is a region where the concentration of a target gas is above an expected background concentration of that target gas. In many situations, the gas plume 112 may be emitted from a source 106. For example, the source may represent a location (e.g., a structure, a geologic feature, a piece of equipment, a component, a certain portion of ground, etc.) that the gas plume 112 is being emitted from. In some applications, the gas plume 112 may be an intended release (e.g. for purposes of characterizing the performance of the measurement system), such as a controlled or metered emission. In some applications, the gas plume 112 may be an accidental release, such as a leak, or an expected release from piece of equipment, often referred to as a process emission.

The lidar system 110 may combine gas concentration measurements with gas flow speed information to determine an emission rate. Various methods may be used to determine a gas flow speed. In some embodiments, the motion of the gas plume may be directly monitored to determine a gas flow speed. In some embodiments, one or more proxy measurements may be used. For example, in many environments the movement of air (e.g., wind speed) may determine the speed and/or direction at which the gas within the plume is moving. Measurements and/or estimates of wind speed at the gas plume 112 may be used to determine the flow speed of the gas plume, which in turn may be used to determine the emission rate. For example, FIG. 1 shows an anemometer 107 used to measure wind speed at a location near the plume source 106, which may act as a proxy for the flow speed of the gas plume 112. In some embodiments, other information (e.g., weather databases, forecasts, information from the mobile platform 101, etc.) may be used instead of or in addition to local sensors such as the anemometer 107. To overcome the impracticality of numerous ground-based anemometers, in some embodiments wind speed measurements may be performed using wind lidar sensor (e.g. potentially aircraft-mounted) to acquire wind speed measurements at altitudes near the ground level and at geographic locations in close proximity to concurrent remote gas concentration measurements. In some embodiments, the plume shape characteristics (e.g. dispersion) may be used to determine gas flow speed.

In some embodiments, one or more components of the lidar system 110 may be spatially separate from one another or located off of the mobile platform 101. For example, the mobile platform 101 may include a sensor system which generates the beam 102, scans it about axis 103, and records measurements of the light received from the scanned area. A remote location may include a computing system which processes the measurements of the sensor system in order to determine emission rates and PoDs. In some embodiments, the sensor system in the mobile platform 101 may be communicatively coupled to the computing system (e.g., via ethernet or wireless communication). In some embodiments the transmission of a laser beam may be spatially separated from the reception of light that has interacted with the environment. In some embodiments the transmission and reception of light may occur from the same aperture. In some embodiments, the measurements taken by the sensor system may be provided to the computing system after a set of measurements are completed (e.g., after the mobile platform has finished scanning a target area). In some embodiments, the sensor measurements may be processed 'live' (e.g., as soon as they are collected). In some embodiments, any portion of the sensor measurements may be processed at a later time.

A scan taken by the lidar system 110 may be characterized by a large number of measurement parameters. Some parameters may be determined based on a chosen measurement procedure, for example, the altitude of the platform 101 above the terrain 105, the speed of the platform 101 relative to the terrain 105, the speed at which the beam 102 is rotated about axis 103, and so forth. Some parameters may be based on the chosen lidar system 110, for example, the strength of the laser beam 102, the size of the angle 104 etc. One or more of these parameters may vary from measurement to measurement or from sensor to sensor. As described in more detail herein, a gas concentration noise measurement may be used to combine a plurality of these parameters into a parameter of lower dimensionality. It may be ideal, for instance, that the detection sensitivity performance of a sensor is knowable based on just two independent variables: the gas concentration noise and the gas flow speed. In addition, physical parameters of the measurement, especially gas flow speed (e.g., wind speed), may also vary between measurements. Accordingly, it may be useful to characterize the performance of the lidar system 110 based on the gas concentration noise measurement and the gas flow rate.

Figure 2:
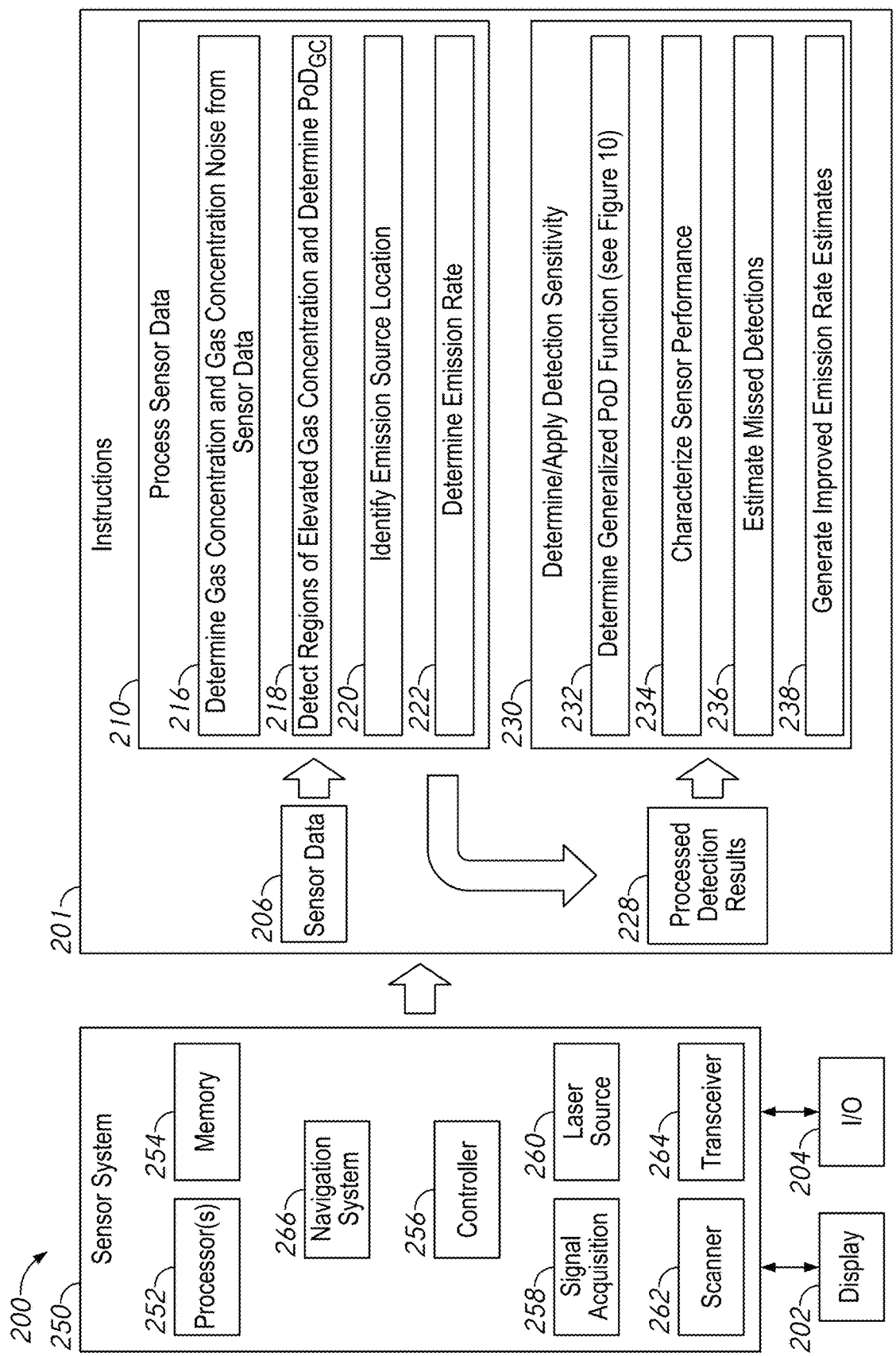
FIG. 2 is a block diagram of a lidar system according to an embodiment of the present disclosure.

FIG. 2 is a block diagram of a lidar system according to an embodiment of the present disclosure. In some embodiments, the lidar system 200 may be used to implement the lidar system 110 of FIG. 1. The lidar system 110 includes a sensor system 250. In some embodiments one or more of these components may be located on a mobile platform (e.g., airplane 101 of FIG. 1). In some embodiments, one or more of these components may be at a remote location (e.g., in an office or lab setting). In some embodiments, certain components may be repeated, for example the sensor system 250 may have an onboard processor and memory, while a computing system used to process the data also has a processor and memory. While a particular distribution of components may be described, any arrangement of components may generally be used. Similarly, it should be understood that the diagram of FIG. 2 may omit certain components (e.g., a power supply) and that some components which are shown in Figure may not be necessary.

The sensor system includes one or more processors 252, a controller 256, and a navigation system 266 all of which may be coupled to a memory 254. The memory 254 includes instructions 201 which may include particular sets of instructions such as block 210 which describes processing sensor data (e.g., as part of a measurement procedure) and block 230 which describes determining and/or applying a determined detection sensitivity function or model. The memory 254 may include one or more other components which may be accessed by one or more of the instructions 201, such as a noise model, gas flow speed information, and/or additional measurements. The sensor system 250 may be coupled to additional components such as a display 202 and an input/output (I/O) device 204 (e.g., keyboard, mouse, touchscreen, etc.).

The sensor system 250 also includes a source 260 (e.g., a laser source) which generates transmitted light, and a scanner 262 (e.g., a rotating mirror) which scans the transmitted light relative to the sensor system to form a transmitted beam (e.g., 102 of FIG. 1). Light from the environment illuminated by the beam is measured by a transceiver 264. A signal acquisition unit 258 may convert raw signals from the transceiver 264 into other forms of data (e.g., by sampling, acting as an analog to digital converter, directing an operation of the transceiver 264, etc.). The sensor system 250 may include additional components (e.g., lenses, mirrors, filters, electronics, etc.) which are not shown in FIG. 2.

While certain blocks and components are shown in the example sensor system 250, it should be understood that different arrangements with more, less, or different components may be used in other embodiments of the present disclosure. For example, while a single processor block 252 is shown in the sensor system 250, multiple processors may be used. In some embodiments, different processors may be associated with different processes of the sensor system 250, such as with different instructions 201 in the memory 254, or with different functions (e.g., a graphics processor, flight plan). While the example sensor system 250 is shown as a single block, it should be understood that the sensor system 250 may be broken up into multiple components such as multiple computing systems. For example, a first computer may be located within or near the sensor system 250 (e.g., a computer on mobile platform 101 of FIG. 1), while a second computer may be at a remote location. The various components of the system 250 may be coupled by any combination of wired and/or wireless connections (e.g., cables, wires, Wi-Fi, Bluetooth, etc.). Similarly, it should be understood that the instructions 201 may be separated in time as well, and may process data from different scanned areas. For example, certain of the steps (e.g., block 210) may happen at a first time, while other steps (e.g., block 230) may represent post-processing and may occur at a later time.

The processor 252 may access the memory 254 to execute one or more instructions 201. Based on the instructions 201, the processor 252 may process measurements from the sensor system 250 (e.g., measurements from the signal acquisition 258). The processor 252 may receive measurements in near real-time from the optical system as the measurements are generated (e.g., measurements may be streamed, provided real-time, or otherwise dynamically transferred), and/or may retrieve measurements 206 which were previously stored in the memory 254. In some examples, the instructions 201 may cause the processor 252 to process the measurements by filtering the measurements, adjusting the measurements, generating new data or flight instructions based on the measurements, and/or storing the measurements in the memory 254. In some embodiments, the processor 252 may process measurements from additional sources, such as from anemometers (e.g., 107 of FIG. 1) to measure the wind speed at a given location which may be used to determine the gas flow speed information. In some embodiments, the additional sources may be external to the sensor system 250. For example, gas flow speed information 228 may be provided by an online weather forecasting system (e.g., a government database, a commercial system). The memory 254 may include additional information such as mathematical constants and mathematical relationships which may be used by one or more of the instructions 201 when executed by the processor 252.

The instructions 201 may include sensor data 206 which is stored in the memory 254. The sensor data may represent raw signals from the signal acquisition unit 258, such as measurements of intensity from the transceiver 264. The instructions 201 include block 210, which describes processing the sensor data to generate processed detection results 228 which may also be stored in the memory 254. Block 210 includes step 216, which describes determining gas concentration and/or gas concentration noise from the sensor data 206. The gas concentration may be generated based on the raw measurements, for example based on principles of optical absorption. For example, the processor 252 may use information about the absorption spectrum of the target gas at the wavelength of the source 260. In some embodiments, the sensor system may determine or verify certain characteristics that ensure the sensor will generate the expected gas concentration signal. For instance, in some embodiments, the sensor system may determine or stabilize the wavelength of the source 260 relative to an absorption spectrum feature of the target gas. In some embodiments, the sensor system may determine a wavelength modulation characteristic of the source 260.

The gas concentration noise may be based on a measured signal-to-noise ratio (SNR) of the gas concentration measurements. The SNR may be determined based, in part on a noise model, and may depend on the light power received by a photodetector in transceiver 264. For example, the measured lidar beam light power and the measured total light power (e.g. ambient plus lidar beam) received by the photodetector for each lidar measurement may be input into a noise model to compute the gas concentration noise for that gas concentration measurement. The gas concentration noise may vary based on various measurement parameters.

The block 210 also includes step 218, which describes detecting regions of elevated gas concentration and/or determining a PoD of one or more regions based on the gas concentration noise ($PoD_{GC}$). The regions of elevated gas concentration may be detected based on various methods, such as by finding different contiguous regions based on the spatial locations of the gas concentration measurements and then determining if those contiguous regions have an elevated concentration. The $PoD_{GC}$ may be calculated based on the gas concentration noise found in step 216 and may be used as an estimate of PoD which in turn may be used to determine a probability of, or confidence in, the detection of the regions of elevated gas concentration. The determination of a $PoD_{GC}$ is optional and may be skipped.

Block 210 includes step 220 which describes identifying an emission source location. For example, once a detected region of elevated gas concentration is found (in step 218) a spatial analysis may be used to determine if an emission source location may be identified for that detection and estimate the location of the emission source. For example, the plume shape, gas concentration data, gas concentration SNR data, gas flow speed, and gas flow direction may be inputted into a computation that employs thresholding and a centroid, or weighted average to determine the emission source location. Other calculations, such as regression methods, may also be used.

Block 210 includes step 222 which describes determining an emission rate. The emission rate may be based on one or more gas concentrations (e.g., from step 216) and gas flow speed information associated with the emission. In some embodiments, a vertical aspect of the gas concentration may be determined and used in an emission rate calculation. A vertical aspect of the gas concentration may be determined using by viewing the same gas plume from multiple perspectives or angles. Each of the gas concentration measurements collected as part of block 216 may have a spatial location in the scene. As part of block 222 a gas flow speed may be applied to one or more of those locations/gas concentration measurements (e.g., based on the source location found in step 220). In some embodiments, a single gas flow speed may be applied to all the gas concentration measurements. In some embodiments, different gas flow speeds may be applied to different of the measurements. In some embodiments, the gas flow speed may be adjusted to account for a height (e.g. of a piece of equipment or a gas plume) or vertical aspect of a gas plume. The memory 254 may store gas flow speed information which may be collected from sensors at or near the scene, determined based on measurements collected from the sensor system 250, based on models or other databases (e.g., weather databases) or combinations thereof.

For example, the gas flow speed information may be based on wind speed information, which may be obtained through the communications module 210 from weather modeling services. Weather modeling services combine observations from multiple weather stations (e.g. around the world with global topographic information and high spatial resolution weather modeling) to provide wind speed and direction data at locations that may not be very near a weather station (known as weather model data), effectively filling in the gaps between the weather station locations. Weather modeling services may offer wind speed and information at a large number of positions on the globe with reasonable temporal resolution. A variety of wind speed and direction data products may be available in the weather model outputs, such as, for example, average speeds and directions for different specified heights above ground as well as gust speeds different specified heights above ground. These services may offer archived wind data such that wind speed and direction information for a particular time and location may be retrieved at a later date for post processing. As the accuracy of weather model data improves and the data resolution increases (both spatially and temporally) these services may become increasingly useful for producing accurate and cost-effective gas flux estimates.

The emission rate may combine the concentration measurement at a location with the gas flow speed information at that location to generate an emission rate (e.g., a gas flux). In some embodiments, multiple gas concentration measurements may be grouped together or spatially reorganized. For example, a raster pattern may be applied to the gas concentration measurements, and an average concentration found within each grid square. Such a process, or other resampling step, may create a uniformly spaced grid of gas concentration measurements, which may aid in other processing steps. A gas flow speed for each grid square may then be found and an emission rate may be determined. The steps of block 210 may generate processed detection results 228.

The memory 254 may include additional instructions which may be useful to characterize the performance of the measurement system over one or more measurement conditions/parameters and/or to use that characterization. The instructions 201 include block 230, which describes using the processed detection results 228 to determine a detection sensitivity and/or to apply that detection sensitivity. For example, the memory 254 may store a generalized PoD function, which characterizes a probability that an emission rate will be detected as a function of gas concentration noise and gas flow speed. The generalized PoD function may be based on, informed by, or validated by measurements collected by the lidar system 200 under metered emission conditions. In some embodiments, multiple generalized PoD functions may be stored, for example based on different ranges of wind and/or gas concentration noise.

The instructions 201 include block 232, which describes determining a generalized PoD function. For example, the lidar system 200 may collect a number of measurements 228 of a known emission source under a variety of conditions (e.g., different emission rates, different gas flow speeds, different measurement altitudes etc.). The measurements may be collected using the steps of boxes 210. The collected measurements may be classified based on whether the known emission was detected or not as well as the gas flow speed and the gas concentration noise associated with the measurement. Based on that classification, one or more PoD functions may be generated, each of which may represent a PoD as a function of emission rate based on either gas concentration noise or flow speed for one or more conditions of the other variable. The PoD function(s) may be used to generate the generalized PoD function. FIGS. 3-11 describe an embodiment of determining the generalized PoD function in more detail.

Block 230 includes optional step 234 which describes characterizing sensor performance. The generalized PoD function may be developed based on measurements of one or more emission sources with known emission rates. During measurements of unknown emission rate, the generalized PoD function may be used to characterize the performance of the system. For example, the generalized PoD function may then be stored in the memory 254 (e.g. as a look-up table or functional form) and then applied to future measurements and/or used to characterize the performance of the measurement system. Alternatively or additionally, measurements of known emission rates may be used to validate one or more points of a general PoD function. For example, the generalized PoD function on its own may be used to determine a lower limit of detection of the measurements or other measure of detection sensitivity performance. For example, a PoD cutoff may be defined and the emission rate which yields that PoD may be determined to represent the lower limit of detection.

In another example of characterizing sensor performance, a histogram or other statistical distribution may be generated based on the number of detected plumes at different emission rates which characterizes the odds that other plumes at that emission rate may have gone undetected. The capability to determine a detection sensitivity may also be used to generate detection statistics for a given survey (e.g. of multiple facilities). As an example, if 1,000 facilities are scanned during a survey, a histogram may be generated showing the frequency of occurrence of facility detection sensitivities that fall into detection sensitivity bins. Alternatively for this example case, a histogram may be generated showing the frequency of occurrence of PoDs for a certain emission rate across the facilities. Such statistics may be used as evidence for the effectiveness or performance of scanning and can be generated for different spatial scales, such as facilities, equipment, pipeline segments, etc. The computing system may display such statistics, for example by graphing a histogram of detection probabilities and outputting it to the display 202. Other example embodiments may use the PoD for other applications, as described in more detail herein.

Figure 12:
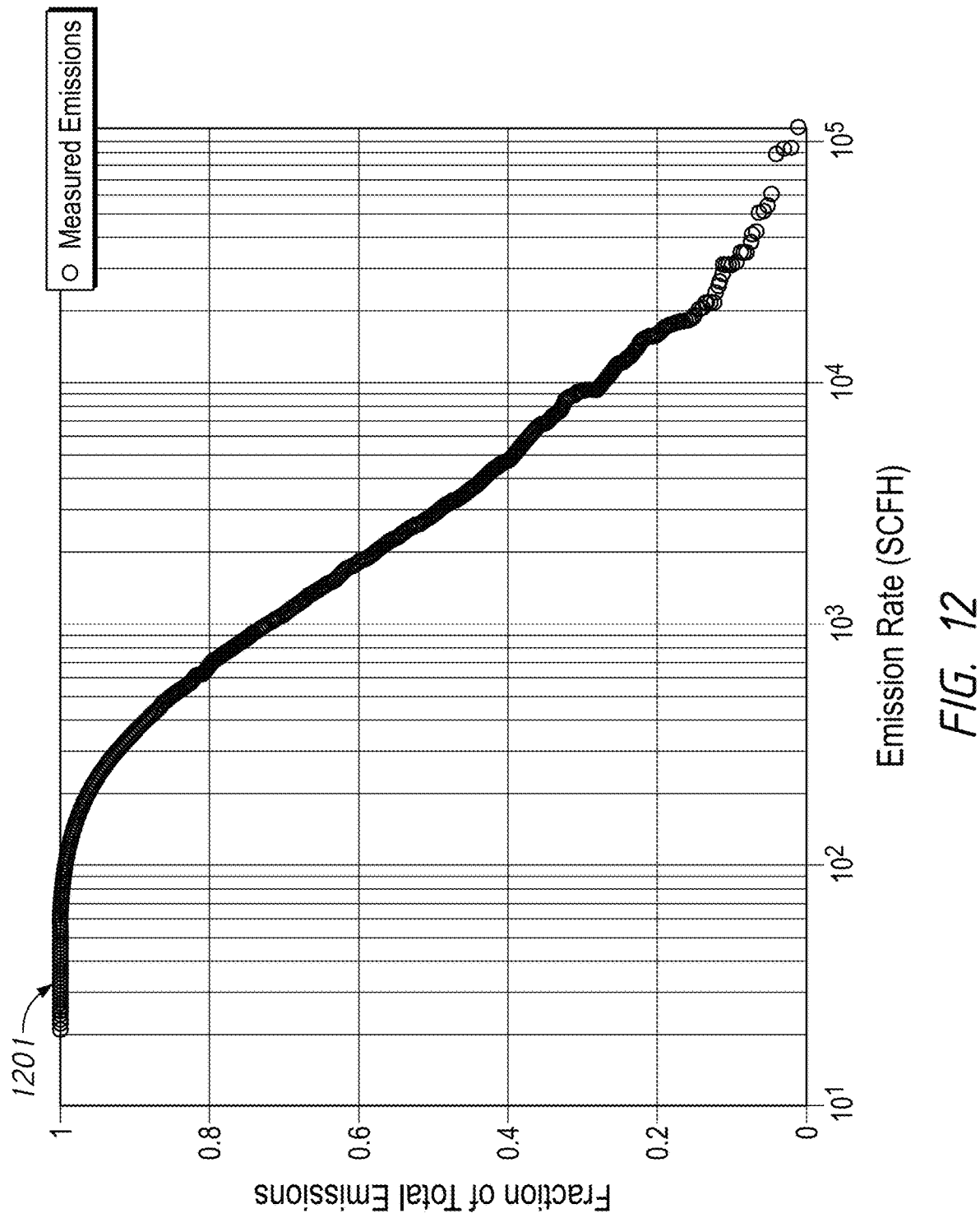
FIG. 12 is a graph of an example cumulative emission rate distribution curve of measured emission rates according to some embodiments of the present disclosure.
Figure 13:
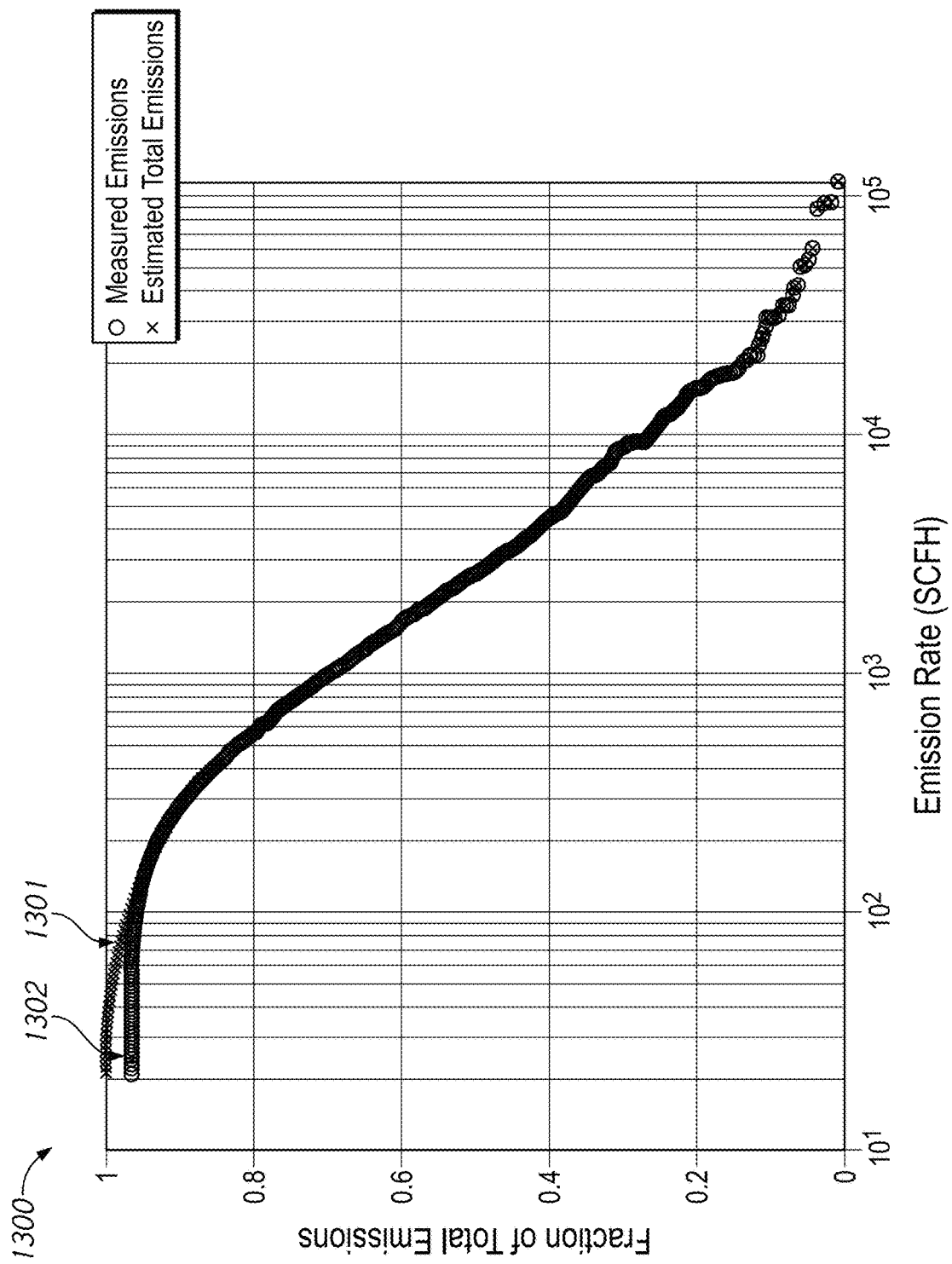
FIG. 13 is a graph of an example estimated cumulative emission rate distribution curve according to some embodiments of the present disclosure.
Figure 14:
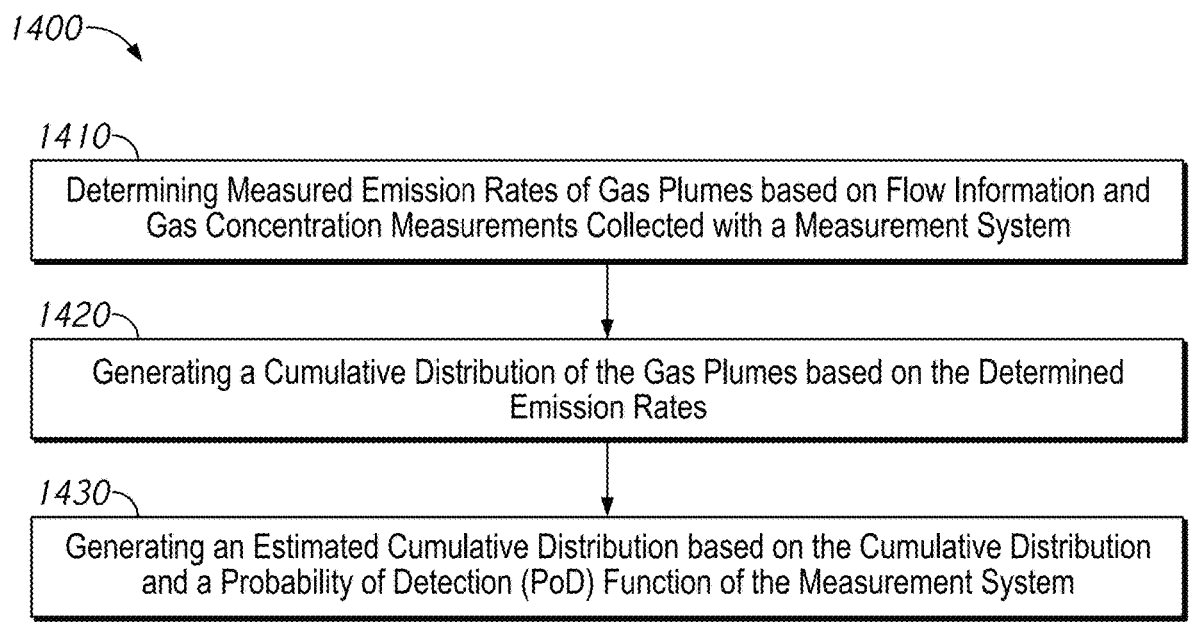
FIG. 14 is a flow chart of a method according to some embodiments of the present disclosure.

Another example application is described by optional block 236, which describes estimating missed detections. A site may be surveyed and a cumulative distribution of detected emission rates (e.g., based on the steps of block 210) may be determined. The generalized PoD function may then be used to estimate the probability that a plume would be detected for the emission rate (based on measured/known gas concentration noise and flow speed). Based on the probability and how many plumes at that emission rate were detected, an estimated cumulative distribution which accounts for estimated missed detections may be generated. FIGS. 12-14 describe an example of estimating missed detections in more detail. Such an estimation of missed detection events may be important for accurate emissions accounting and emissions inventories.

Figure 15:
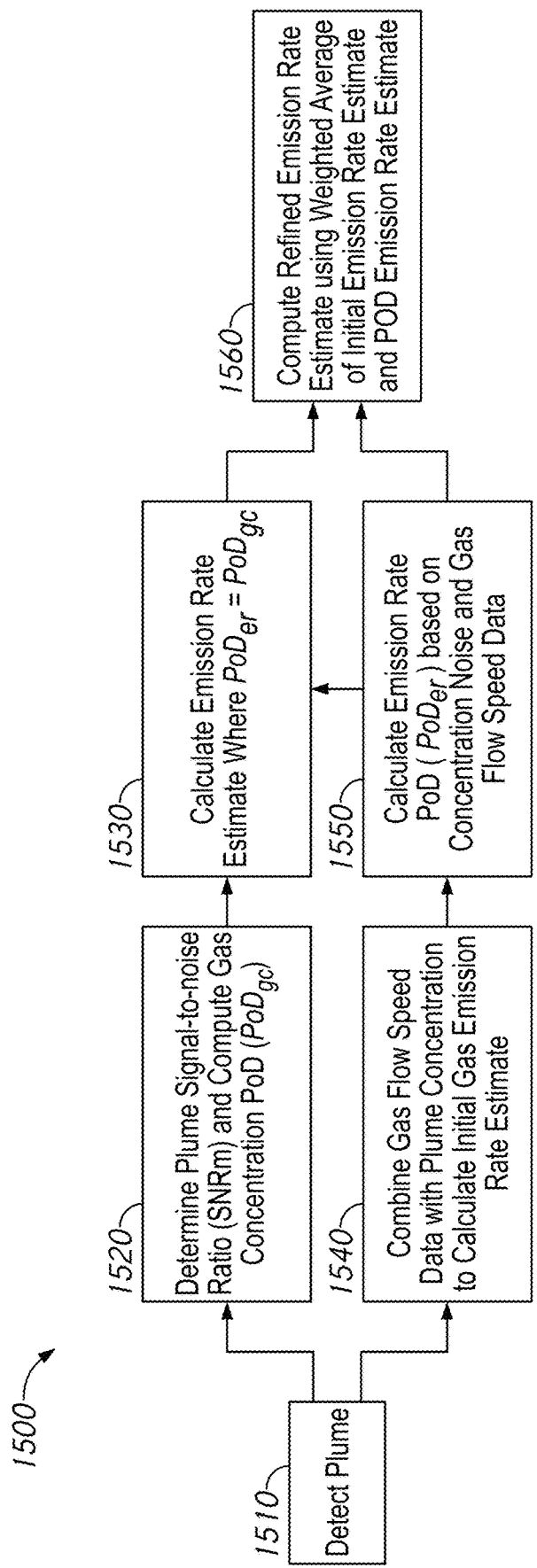
FIG. 15 is a flow chart of a method for computing an improved emission rate estimate by comparing the emission rate PoD and the gas concentration PoD for a detected gas plume according to some embodiments of the present disclosure.
Figure 16:
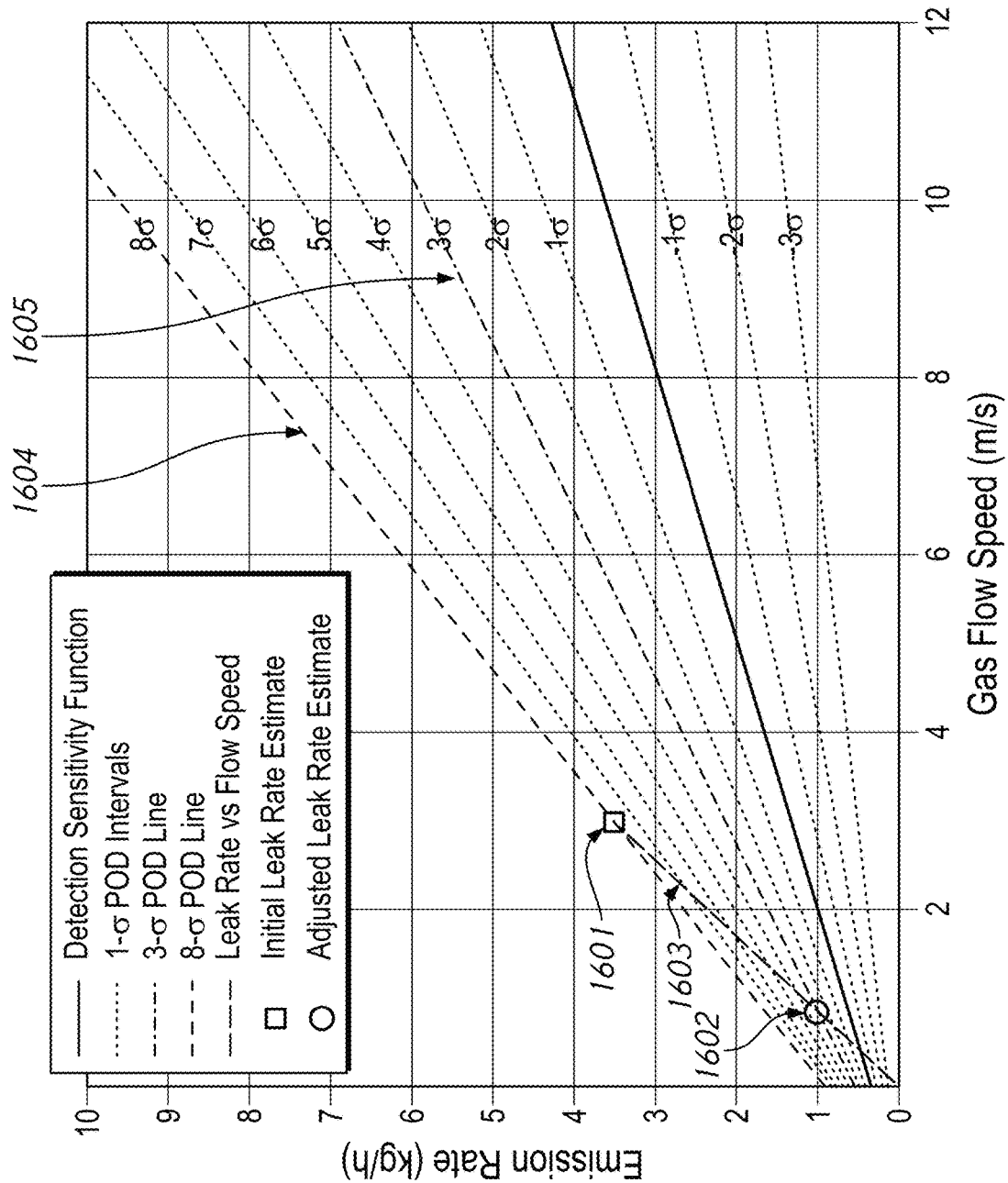
FIG. 16 is a graph which shows an example method for adjusting gas flow speed estimate based on a comparison of the emission rate PoD and the gas concentration PoD according to some embodiments of the present disclosure.

Another example application is described by optional block 238, which describes generating improved emission rate estimates. Based on the generalized PoD function and the emission rate and gas concentration noise a PoD based on emission rate (e.g., $PoD_{ER}$) may be determined. The $PoD_{ER}$ may be compared to the $PoD_{GC}$ (e.g., from block 218). Based on that comparison, an estimated flow speed (and thus an estimated emission rate) may be determined for example to match $PoD_{GC}$ and $PoD_{ER}$. FIGS. 15-16 describe an example of generating an improved emission rate estimate in more detail.

The computing system 201 may also be coupled to one or more external components, such as a display 202 and an input/output device (I/O) 204. In some embodiments, the display 202 may be used to display one or more pieces of information, such as a gas plume image, which may take the form of a map of the gas concentration measurements in space. In some embodiments, the gas plume image may be overlaid on a representation of the environment (e.g., an aerial image of the environment, a map of the environment, topographic information about the environment, etc.). In some embodiments, the I/O 204 may allow a user to control one or more operations of the computing system 201. For example, the user may be able to select a source of the wind speed measurements (e.g., from different sensors and/or from different external services).

FIGS. 3-11 describe aspects of an example procedure for determining a generalized PoD function (e.g., box 232 of FIG. 2). The steps of FIGS. 3-11 may be implemented by the lidar system 110 of FIGS. 1 and/or 200 of FIG. 2 in some embodiments. In describing the features of FIGS. 3-11, reference may be made to the components and reference numbers of FIGS. 1-2. All of the graphs of FIGS. 3-10 show example data including specific numbers, ranges, values, etc. It should be understood that these are shown for illustrative purposes only, and that any number, range or value may be used.

The generalized PoD function may be developed based on measurements of known (e.g. metered) emissions. From those measurements false negative and true positive detection events may be determined. Based on those determinations, one or PoD functions with respect to emission rate may be generated. Those PoD functions may be based on which measurements detected the gas plume (true positive) and which did not (false negative), as well as the conditions of the measurement (which may be controlled, normalized, or otherwise accounted for). From those PoD functions, the generalized PoD function may be developed.

In an example measurement procedure for determining the generalized PoD function, an aircraft 101 carrying a gas concentration lidar remote sensor 110 performs successive scans of a controlled release location 106. The controlled release location 106 releases gas at a known emission rate. The lidar beam 102 is spatially scanned to acquire gas concentration imagery of the area near the controlled release location. In this embodiment the spatial scanning is achieved by rotating the lidar beam about the nadir direction 103 to create a fixed field of view conical scan that creates a scan area as the aircraft motion moves the conical scan pattern over the terrain below the aircraft. The controlled release location is outfitted with a system for releasing gas at a known mass flow rate to generate a gas plume 112, and an anemometer 107 for measuring the wind speed and direction near the location of the released gas plume. This may yield a known gas emission rate and a known gas flow speed (e.g., from the anemometer 107 data) which may be used to compute the PoD at different gas flow speeds. The measurement conditions such as flight altitude, flight speed, scan rate, etc. may also be controlled and taken into account. For example, each scan may be performed at a fixed flight altitude and then repeated at a different flight altitude. The gas concentration noise may be measured for any measurement conditions.

As part of measuring the known emissions, a test plan may be used which specifies one or more measurement conditions. For example, a test plan may be developed to define the controlled release mass flow rate issued for each successive scan. The test plan may define varying magnitudes of mass flow release rates for different wind speeds at the controlled release location. Lidar sensor data acquired during the controlled release test scanning may be processed to determine a gas concentration and distance to the topographic backscatter target for each lidar measurement. Navigation system data (e.g., from 266 of FIG. 2) may be combined with the lidar range measurement data to determine a geo-registered location for one or more lidar gas concentration measurements. Measurements from different angles may be used to determine a vertical profile of a gas plume.

A noise model for the gas concentration lidar measurements may be used to determine an uncertainty parameter associated with one or more lidar measurements, such as a gas concentration noise. The gas concentration noise may account for various measurement parameters. Equation 1 shows an example lidar gas concentration noise model where the noise associated with a lidar measurement ($n_{conc}$) includes contributions from detector noise ($n_{dn}$), speckle noise ($n_{spn}$), and shot noise ($n_{sn}$).

$$n_{conc} = \sqrt{n_{dn}^2 + n_{spn}^2 + n_{sn}^2}. \quad \text{Eqn. 1}$$

Attributes of each lidar gas concentration measurement, such as the received lidar beam power and received total light power (e.g. lidar beam plus ambient) may be inputted into the gas concentration noise model to compute a gas concentration noise value for each lidar gas concentration measurement. Other sources of noise may be included in the noise model if they represent non-negligible contributions to the noise or as appropriate/desired to the particular remote sensor. A statistical algorithm may be applied to the lidar gas concentration measurements to determine if a spatial region of elevated gas concentration (e.g. a gas plume) is detected near the controlled release location. If a region of elevated gas concentration is detected the algorithm may determine the extent of the region of elevated gas concentration and an associated probability of detection (PoD) based on the signal-to-noise ratios of lidar gas concentration measurements with the region of the detected gas plume.

Figure 3:
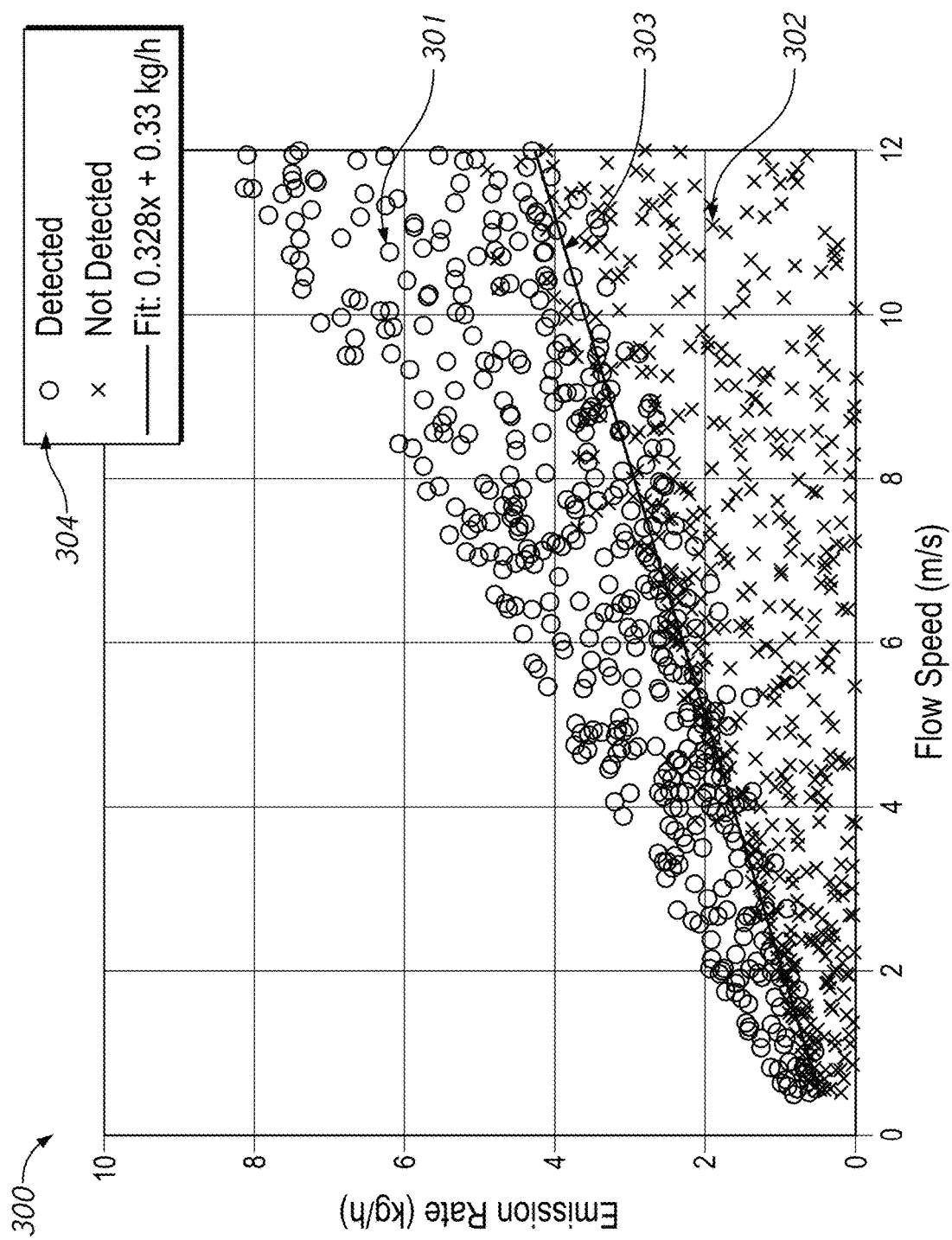
FIG. 3 is a graph of measured controlled emission rates for possible detection by a lidar system according to some embodiments of the present disclosure.

FIG. 3 is a graph of measured controlled emission rates for possible detection by a lidar system according to some embodiments of the present disclosure. The graph 300 represents data which may be used to determine a sensitivity function. The sensitivity function in turn may be useful to determine PoD functions which are used to generate the generalized PoD function. The graph 300 shows flow speed across the horizontal axis and released emission rate across the vertical axis. Each point represents an experimental condition where the controlled source emitted the gas at a known emission rate plotted against a windspeed measured by an anemometer at the time of the measurement. These measurements may be used to determine a sensitivity function (and/or PoD function as described in more detail herein).

FIG. 3 shows example measurement outcomes from controlled emission rate test data acquired using airborne lidar gas sensor. For each scan of the emission location, a gas plume of known emission rate is released and the wind speed near the plume location is measured. Acquired gas concentration lidar measurements are processed using a statistical algorithm to determine if a region of elevated gas concentration (e.g., methane concentration) is detected near the release location. For example, the lidar measurements may be processed to determine if there is a detected gas plume (e.g., a region of elevated gas concentration) present (e.g., using the steps of block 210 of FIG. 2). The measurements may be classified as 'detected' if the lidar system properly determined that there was a detected gas plume or 'undetected' if a gas plume was not detected by the lidar system. For example, thresholding may be used (adaptive and/or fixed) to determine if a region near the controlled release location has elevated gas concentration or other methods may be used to detect the plumes.

The controlled release rate and measured wind speed for detected emissions 301 and undetected emissions 302 are fit using an emission rate detection sensitivity function 303 to determine a 50% sensitivity function as a function of wind speed for a specific set of emission rate detection sensitivity measurement conditions (e.g., the type of lidar system used, the type of mobile platform used, the elevation/speed of the mobile platform, scan rate, etc.). While 50% is used as a metric for this example, any percentage may be used to determine the sensitivity function.

An example set of data from controlled release flyover measurements for determining the emission rate detection sensitivity of gas concentration lidar measurements is shown in FIG. 3. The mass flow rate of the controlled gas releases is plotted against the wind speed measured by the anemometer 107. Controlled release plumes that were detected (e.g. true positive detection) through application of the detection algorithm to the lidar gas concentration measurements are represented by the symbol 'o' (301), and plumes that were not detected (e.g. false negative detections) are represented by the symbol 'x' (302).

The test data, 301 and 302, may be fit with a detection sensitivity function 303. The fit routine may optimize the detection sensitivity function parameters by minimizing an error function comprising the sum of squared errors of detection data points, 301 and 302, located on the 'wrong' side of the detection sensitivity function line. In this case, the wrong side of the detection sensitivity function refers to detected emissions 301 located below the detection sensitivity function line 303, and non-detected emissions 302 located above the detection sensitivity function line 303. In the limit of large numbers of flyover measurements, with emission rates spanning the range from not detected to detected, the detection sensitivity function may represent the 50% probability of detection emission rate for a given set of measurement conditions (e.g. wind speed, lidar return power, background light, lidar point density, and/or other parameters). The example detection sensitivity function 303 is a linear function, $$\phi_n(v) = mv + b, \quad \text{Eqn. 2}$$

where $\phi_n(v)$ is the emission rate detection sensitivity as a function of wind speed for measurements with concentration noise n, v is the wind speed and m and b are linear polynomial coefficients. Other functional forms for the emission rate detection sensitivity function may be used. An emission rate detection sensitivity function may include any function, look-up table, or similar information representing detection events, for any probability, versus gas flow speeds (e.g. wind speeds).

Figure 4:
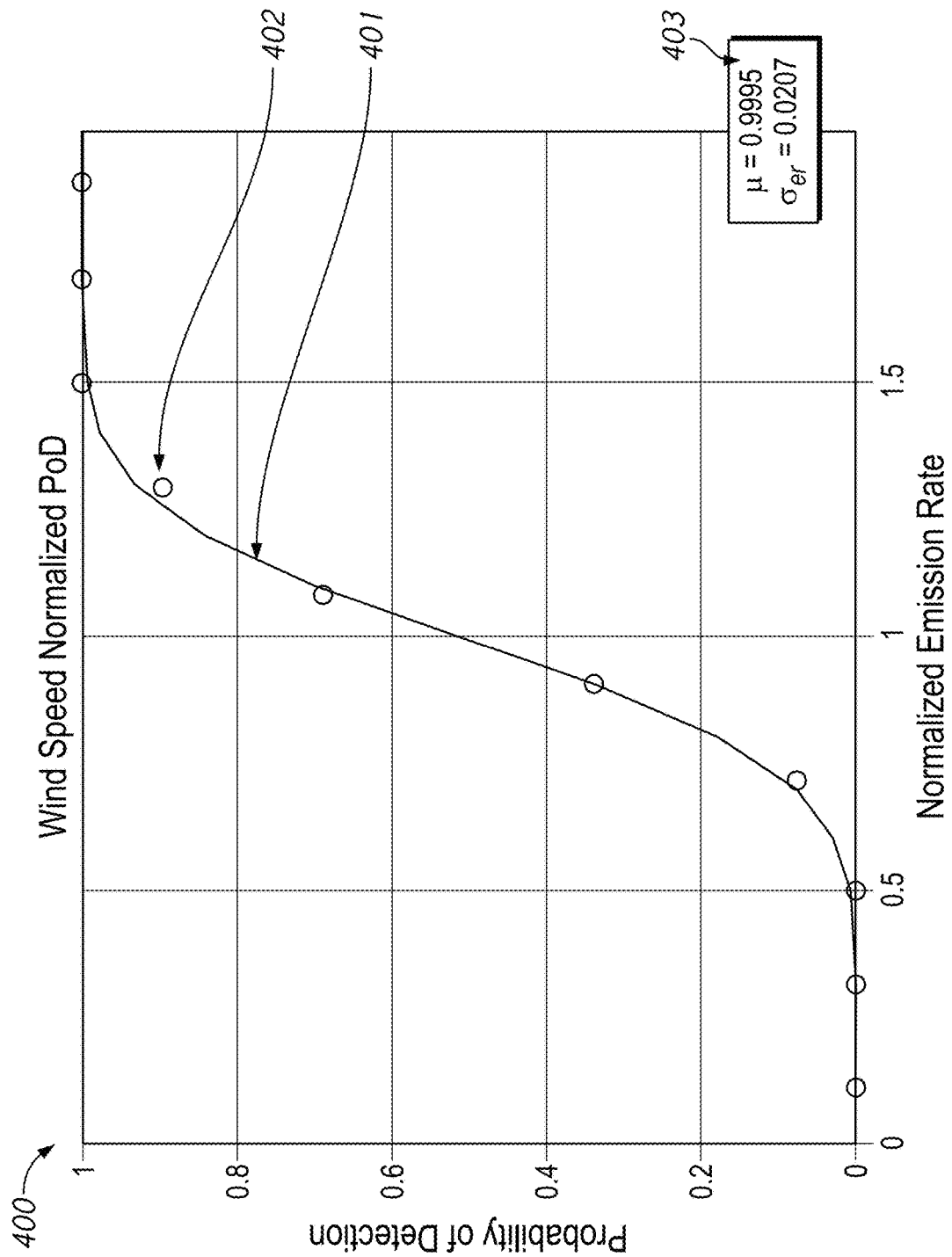
FIG. 4 is a graph of an example probability of detection versus normalized emission rate function.
Figure 5:
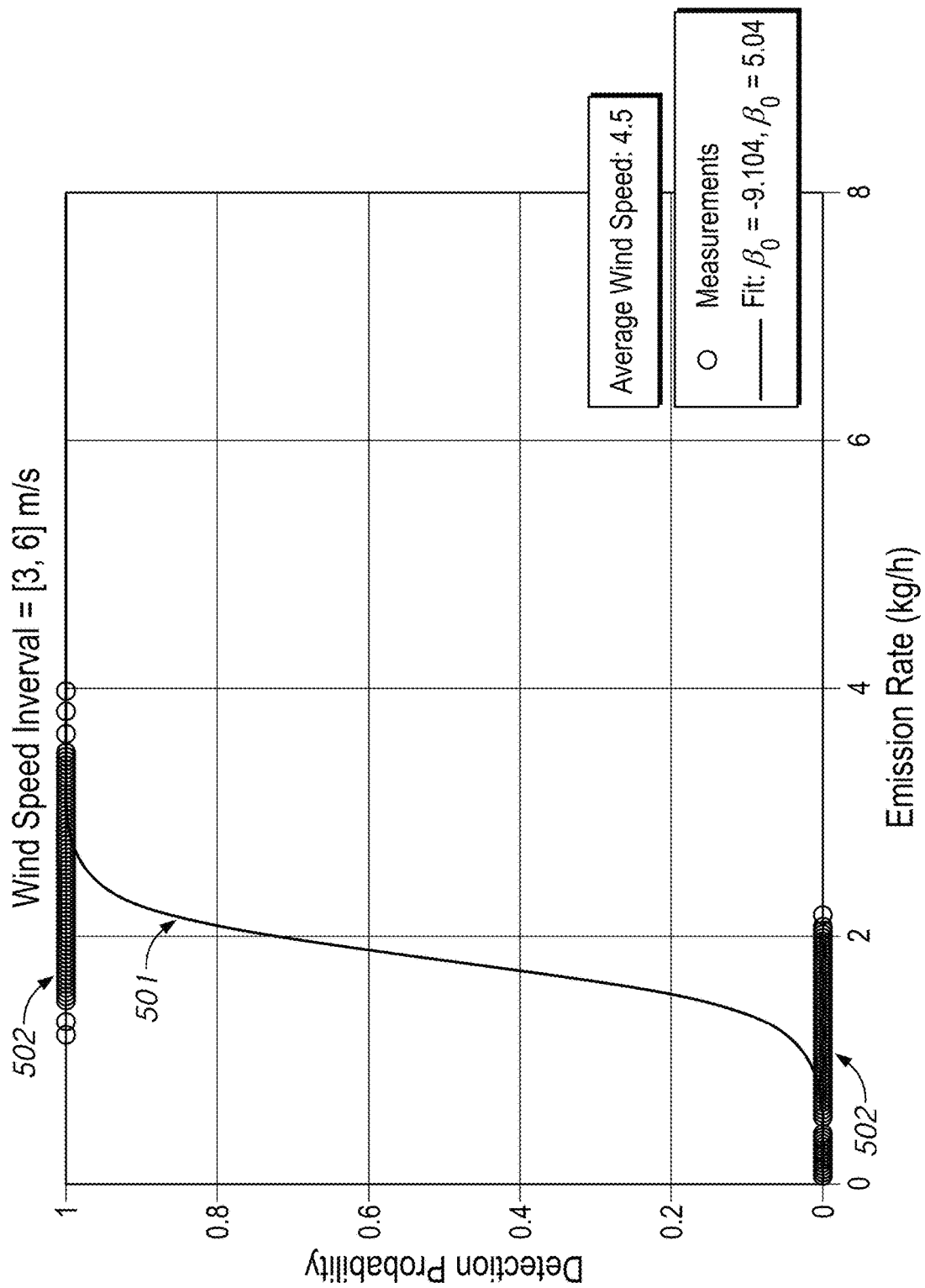
FIG. 5 is a graph of a logistic regression used to generate a PoD vs emission rate according to some embodiments of the present disclosure.
Figure 6:
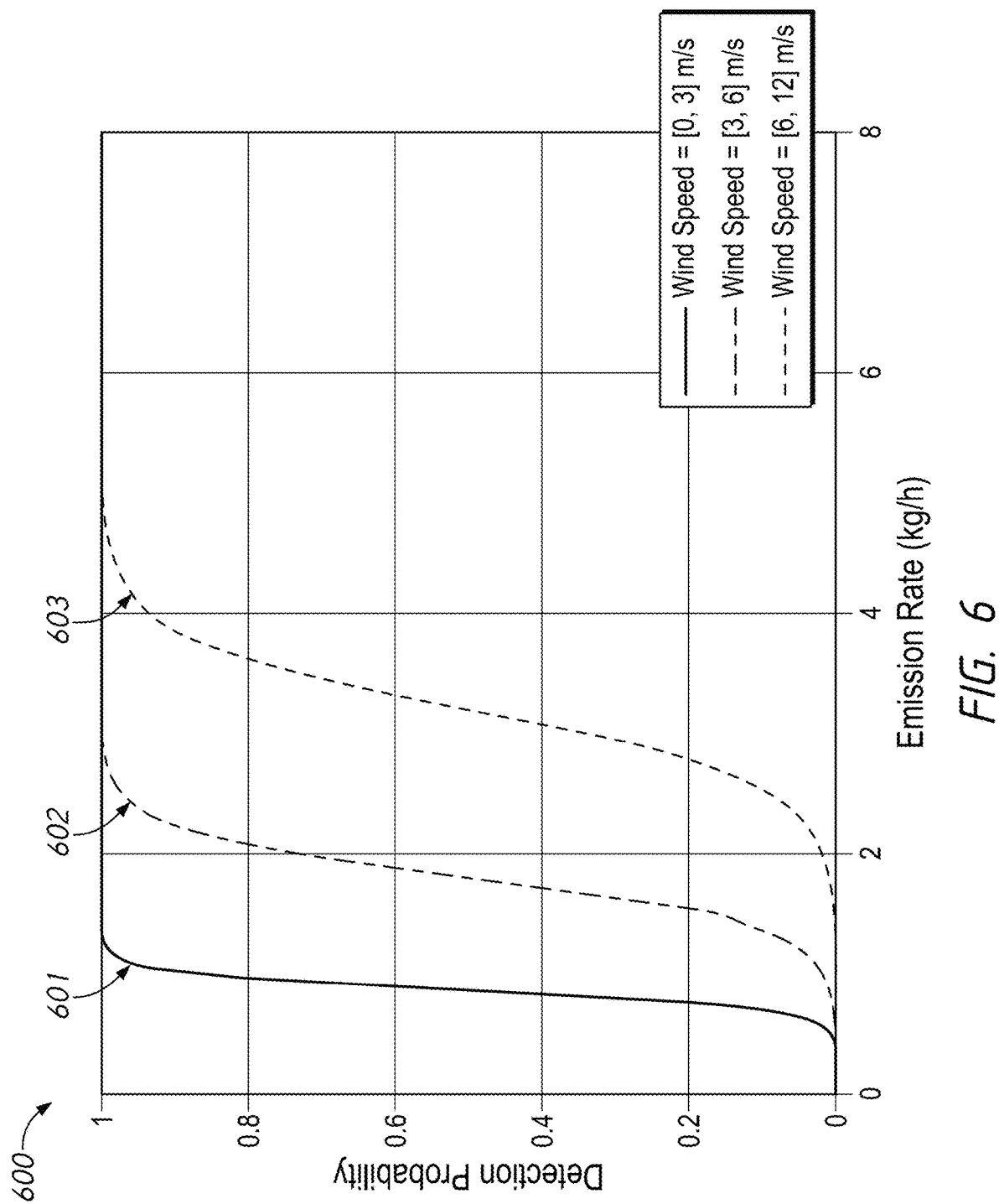
FIG. 6 shows a number of a graphs of different PoD functions each of which is plotted for data across a different wind speed interval according to some embodiments of the present disclosure.

The example detection sensitivity function $\phi_n$ is expressed with respect to the gas concentration noise n, because at other gas concentration noises the gas sensitivity function may be different. The measurements of the graph 300 may represent measurements taken with similar gas concentration noise. FIGS. 4-6 show examples of how information such as the detection sensitivity function 303 may be used to develop one or more PoD functions with respect to emission rate based on flow speed when gas concentration noise is held constant or otherwise normalized/accounted for.

FIG. 4 is a graph of an example probability of detection versus normalized emission rate function. The graph 400 represents one method of generating a PoD function which may be used to generate a generalized PoD function in some embodiments. The graph 400 shows a normalized emission rate along the horizontal axis and the probability of detection along the vertical axis. FIG. 4 represents an example PoD function which may be generated from the controlled emission rate data discussed with respect to FIG. 3.

The probability of detection data points 402 may be determined from emission rate detection sensitivity measurements such as the ones shown in the graph 300 of FIG.

3, using the following steps: 1) determine the normalized emission rate of each gas release by dividing each controlled release gas emission rate by the emission rate sensitivity function at that flow speed, 2) select a range of flow speeds over which a probability of detection function is applicable or desired, 3) generate histograms of the detected releases and total releases in a specified number of normalized emission rate bins within the selected range of flow speeds, and 4) compute the probability of detection within each normalized emission rate bin using equation 3—divide the number of detected releases by the number of total releases in each bin.

$$P_{bin} = \frac{N_{det}}{N_{pts}} \qquad \text{Eqn. 3}$$

Here, $P_{bin}$ is the detection probability for each normalized emission rate bin, and $N_{det}$ and $N_{pts}$ are the number of detected plumes and total number of controlled release measurements within each normalized emission rate bin, respectively. A cumulative distribution function (CDF) may be fit to the normalized emission rate probability of detection data 402 to derive cumulative distribution function fit parameters 403. In the example shown in FIG. 4 the emission rate probability of detection (PoD) data was fit with an error function $$p(x) = \frac{1}{2}\left(1 + \text{erf}\left(\frac{x-\mu}{\sqrt{2}\,\sigma_{er}}\right)\right), \qquad \text{Eqn. 4}$$

where p(x) is the probability of detection, x is the normalized emission rate, μ is the mean of the normalized emission rate distribution, and $\sigma_{er}$ is the standard deviation of the normalized emission rate distribution. Other functional forms may also be used (e.g. to represent the probability of detection as a function of emission rate). For the fit shown in FIG. 4 μ=0.9995 and σ=0.20692, however these are example values based on the example data set discussed herein and other fit values may be used based on other data sets. The PoD function may vary with wind speed as shown in FIG. 4 and/or may vary with gas concentration noise, as discussed in more detail herein.

Possible variations may include changes in the standard deviation versus wind speed or even changes in the PoD functional form versus wind speed. If PoD parameters or functional form variation as a function of wind speed is observed, independent probability of detection functions 401 may be generated for different wind speed intervals. This may be accomplished by first splitting the detection data 301 and 302 into the desired wind speed intervals, then determining probability of detection data 402 for each wind speed interval, and finally, performing a separate cumulative distribution function fit to the probability of the detection data 402 for each wind speed interval. For example, FIG. 6 shows examples of different PoD functions based on different wind speed intervals.

FIG. 5 is a graph of a logistic regression used to generate a PoD vs emission rate according to some embodiments of the present disclosure. The graph 400 of FIG. 4 represents one method of generating a PoD function. Aside from, or in addition to, the fitting discussed with respect to FIG. 4, other techniques may also be used to determine an emission rate vs. PoD function. One of these may be to use a logistic regression as shown in the example of FIG. 5. The logistic regression shown in the graph 500 of FIG. 5 represents an alternative method of generating a PoD function which may be used to generate the generalized PoD function.

A logistic regression is a form of generalized linear model that fits a logistic sigmoid function to a set of data with a binary dependent variable, in this case detection and non-detection events 502, and a continuous independent variable, in this case emission rate. FIG. 5 shows a plot of the selected ones of the detected 301 and non-detected 302 emission data points from FIG. 3. The selected ones may be selected based on a range or interval of gas flow speeds (e.g., wind speed interval), gas concentration noise, or other parameter. In the example of FIG. 5, a wind speed interval is chosen, and so the PoD generated from FIG. 5 may be valid across that wind speed interval.

Individual release events are plotted with a detection probability of '1' (e.g., the release was detected), while the non-detection events are plotted with a detection probability of '0' (e.g., the release was not detected). The logistic regression sigmoid function may take the form, $$p(x) = \frac{1}{1 + e^{-(\beta_0 + \beta_1 x)}}. \qquad \text{Eqn. 5}$$

Here, p(x) is the probability of detection, x is the emission rate, and $\beta_0$ and $\beta_1$ are the fit coefficients. An example logistic regression PoD function 501 is shown in FIG. 5. In this example, the emission rate is not normalized to unity. Instead, measured emission rates are normalized to an emission rate having the equivalent PoD at the average wind speed for the data set being fit with the regression. Emission rate normalization to the average wind speed may be performed using the slope of the sensitivity function (e.g. similar to the one shown in FIG. 3) evaluated at the average wind speed for the data set being fit. A Taylor expansion of the detection sensitivity function may be used to generate the detection sensitivity slope in the vicinity of the average wind speed and evaluate the normalized emission rate, $$\varepsilon_{norm} = \varepsilon_m - \left.\frac{\partial \phi_n(v)}{\partial v}\right|_{v=v_{avg}} (v_m - v_{avg}). \qquad \text{Eqn. 6}$$

Here, $\varepsilon_{norm}$ is the normalized emission rate, $\varepsilon_m$ is the controlled release emission rate, $v_m$ is the measured wind speed associated with each controlled release emission rate, $v_{avg}$ is the average wind speed of the controlled release data being fit with the regression, and $$\left.\frac{\partial \phi_n}{\partial v}\right|_{v=v_{avg}}$$

is the slope of the sensitivity function evaluated at the average wind speed.

Like the CDF fit method discussed with respect to FIG. 4, the logistic regression of FIG. 5 may be used to evaluate emission rate PoD functions for different wind speeds, as shown in FIG. 6, by splitting the detection data 301 and 302 of FIG. 3 into sets corresponding to the desired wind speed intervals.

Other methods may also be used to generate a PoD function. In some embodiments, a signal-to-noise ratio (SNR), or other metric of true positive detections may be used to estimate a detection sensitivity function without collecting false negative information. For instance the SNR of true positive detections may be used to determine (e.g. by extrapolating or fitting the behavior versus known emission rate) a detection limit for measurement conditions (e.g. a wind interval), which is a form of PoD function (e.g. a step function).

FIG. 6 shows a number of a graphs of different PoD functions each of which is plotted for data across a different wind speed interval according to some embodiments of the present disclosure. The PoD functions may represent PoD functions which are useful at different ranges of flow speed (here expressed as wind speed). FIG. 6 shows a graph 600 of PoD functions, each plotted as a function of emission rate. Each of the functions is based on data collected within a wind speed interval. The three functions may be generated based on curve fitting (e.g., as discussed with respect to FIG. 4), logistic regression (e.g., as discussed with respect to FIG. 5), and/or any other method.

For example, a logistic regression may then be applied to each of detection data sets to generate separate emission rate PoD functions (601, 602, 603) for each wind speed interval. The three windspeed intervals shown in FIG. 6 ([0, 3] m/s, [3, 6] m/s, and [6, 12] m/s) are non-overlapping intervals. Overlapping wind speed intervals may also be used to evaluate the PoD function dependence on wind speed with higher resolution. Refined estimates for the sensitivity function fit parameters or even functional form may be derived from the wind-speed-resolved PoD functions. The refined detection sensitivity function may then be used to determine improved normalized emission rates, followed by another CDF fit or logistic regression step to generate refined PoD functions. This iterative optimization process may be continued until the detection sensitivity function and PoD functions converge on a stable and self-consistent set of results.

Figure 7:
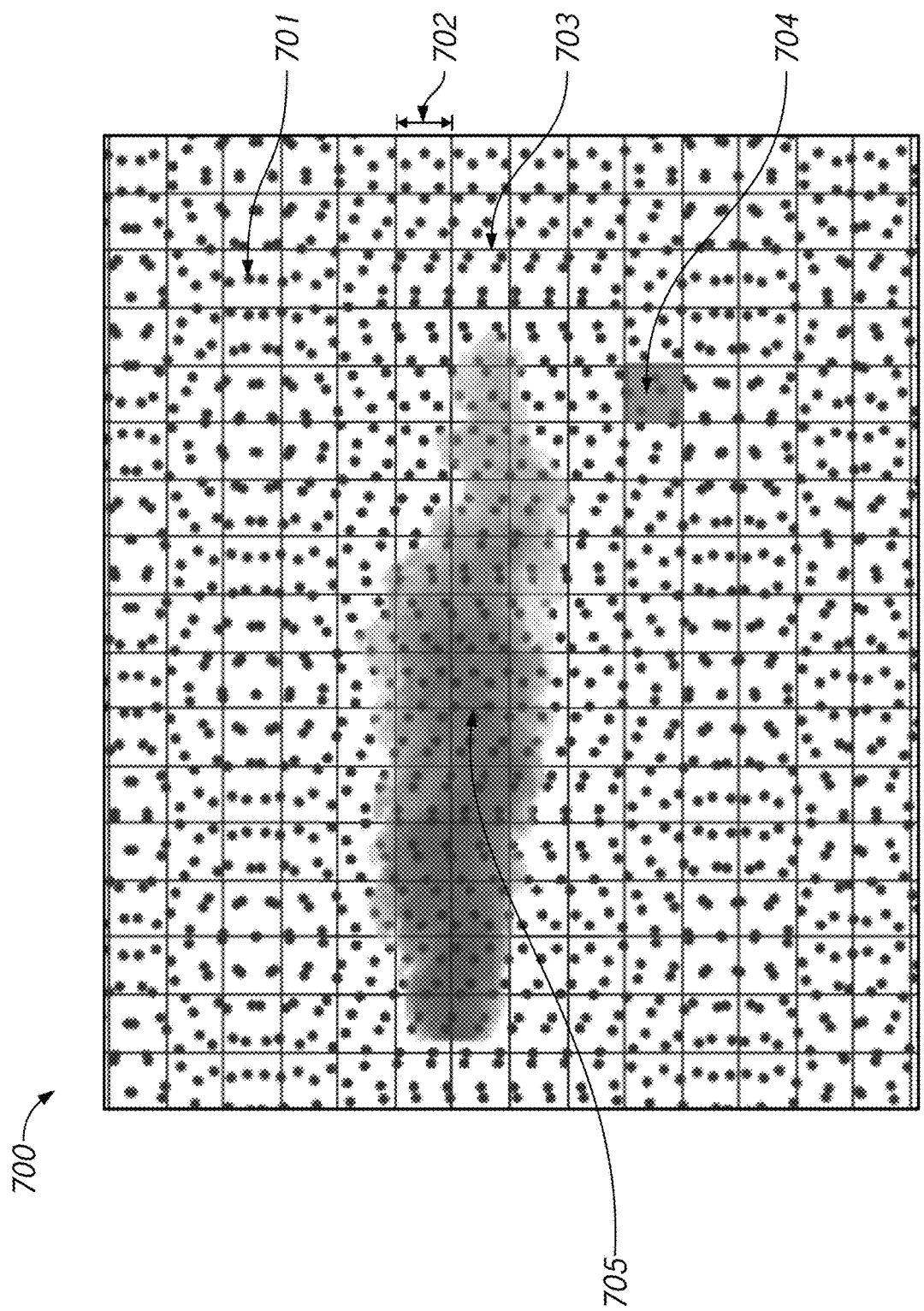
FIG. 7 is a graph of a scan pattern according to some embodiments of the present disclosure.
Figure 8:
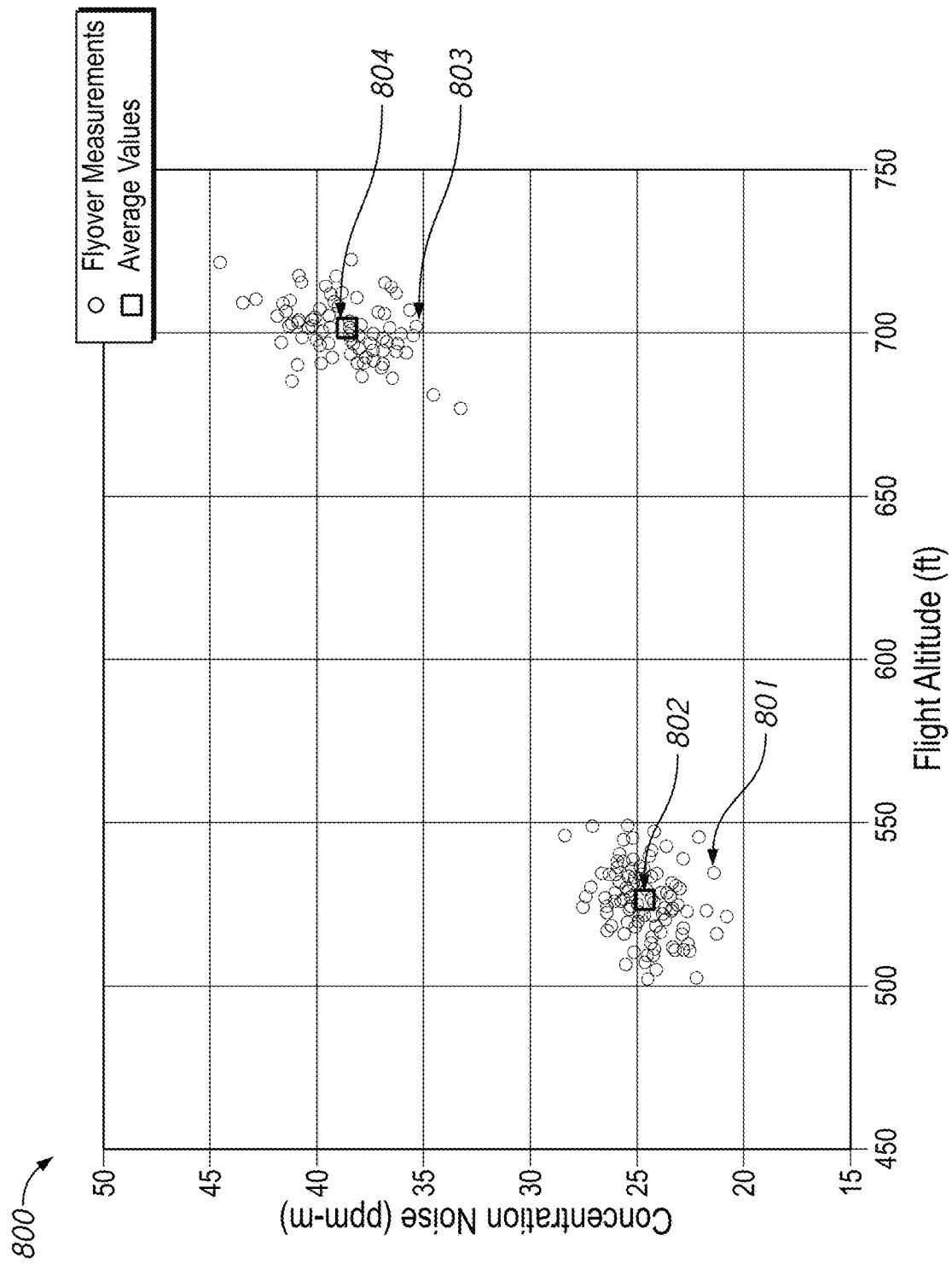
FIG. 8 is a graph of determining gas concentration noise as a function of different measurement conditions according to some embodiments of the present disclosure.
Figure 9:
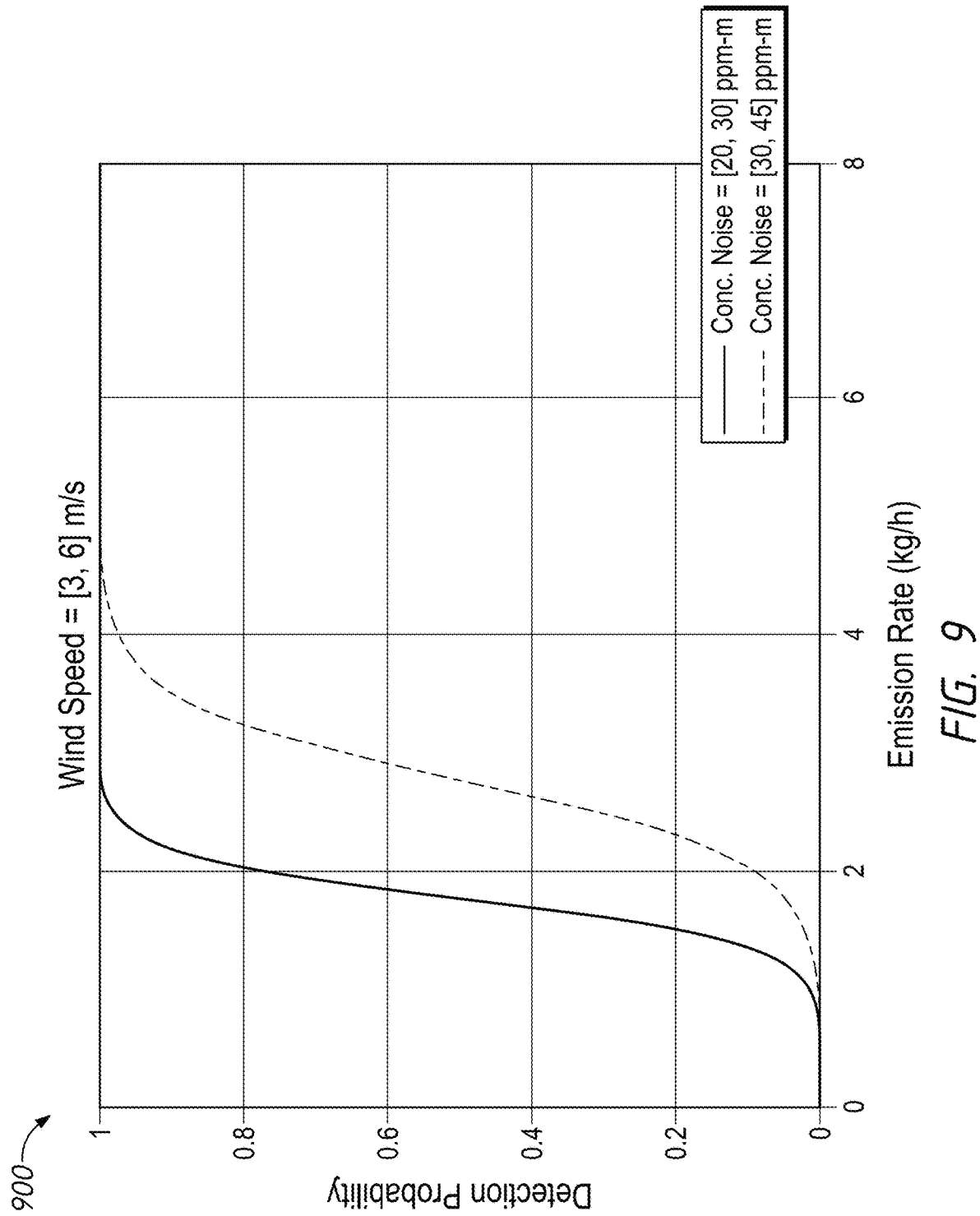
FIG. 9 is a graph of different PoD functions plotted for different ranges of gas concentration noises according to some embodiments of the present disclosure.

FIGS. 7-9 show examples of how gas concentration and gas concentration noise may be computed for a grid of defined spatial extent, how different measurement conditions may affect the gas concentration noise, and how that may be used to generate one or more PoD functions with respect to emission rate which vary based on the gas concentration noise in a manner analogous to the PoD functions which vary based on flow speed discussed with respect to FIGS. 4-6.

FIG. 7 is a graph of a scan pattern according to some embodiments of the present disclosure. The graph 700 shows a spatial distribution of measurement points 701 as a mobile platform (e.g., mobile platform 101 of FIG. 1) moves across an area while scanning a beam (e.g., 102). For example, the graph 700 may represent a pattern collected by a lidar system (e.g., 200 of FIG. 2) as it scans an area. FIG. 7 shows an embodiment where different measurements may be spatially grouped to allow for spatial averaging of measurements and/or resampling onto a grid pattern to represent the concentration data as a raster image.

The graph 700 shows an example interpolation of lidar scan data 701 onto a regular grid with pixel size 702 and pixel boundaries 703. Other methods including but not limited to binning, histogram, scattered interpolant, or weighted average may be implemented to determine the gas concentration and gas concentration noise (e.g. measurement uncertainty) associated with each pixel 704. Regions containing a gas plume 705 are characterized by elevated values for the ratio of the gas concentration to gas concentration noise (e.g. gas measurement SNR). Furthermore, the probability of detecting gas plume 705 may be computed based on the ratio of the gas concentration to the gas concentration noise using individual lidar point measurements and/or spatially grouped or gridded measurements.

The scan pattern of the graph 700 shows an example of how different measurement parameters may change the gas concentration noise. For example, if the movement of the airplane was faster relative to the ground, there would be fewer measurements 701 per grid square. This in turn would affect the amount of measured signal per grid square, which would decrease the SNR and raise the gas concentration noise. Other changes to the measurement parameters may similarly affect the gas concentration noise.

A generalized relationship between the emission rate detection sensitivity and the lidar gas concentration measurement noise may be established to extend the emission rate probability of detection results derived in the previous section, which are valid for a specific value of gas concentration noise, to any measurement acquired by the remote gas sensor, acquired under any operational conditions (e.g. flight speed, flight altitude, ground reflectivity, etc.). This section presents an example method for establishing such a relationship. First, individual lidar gas concentration measurements 701 may be interpolated onto a regular grid to form a gas concentration raster data layer with pixel size 702 by defining grid boundaries 703 that specify the area covered by each pixel 704 within the grid. A weighted (or unweighted) average may be performed on the lidar gas concentration measurements $c_i$ within each pixel to determine the gas concentration assigned to that pixel. The weighted average gas concentration assigned to the $j^{th}$ pixel $c_j$ may be found by $$c_j = \frac{\sum w_i c_i}{\sum w_i}, \quad \text{Eqn. 7}$$

where $w_i$ is the weight applied to the $i^{th}$ lidar gas concentration measurement within the $j^{th}$ pixel. The weights $w_i$ may be determined using the noise estimate generated using the gas concentration noise model in Equation 1 to give Equation 8, below, $$w_i = \frac{1}{n_i^2} \quad \text{Eqn. 8}$$

The noise associated with the weighted average gas concentration assigned to the $j^{th}$ pixel may be generated by $$n_j = \frac{1}{\sqrt{\sum w_i}} \quad \text{Eqn. 9}$$

Other (or no) weighting methods and/or equations may also be used.

This method of interpolating gas concentration lidar measurements onto a grid may yield a statistical estimate of gas concentration for each pixel (e.g., each grid square) with an uncertainty estimate (e.g., the gas concentration noise) that accounts for factors that determine detection sensitivity including detector noise, received optical power, background light, lidar point density, ground surface reflectivity, flight altitude, flight speed, and/or other parameters. This may be useful for characterizing a performance of the system as it may consolidate multiple different environmental and/or operational parameters into one, or a small number of measurable or known parameter (e.g. gas concentration noise).

FIG. 8 is a graph of determining gas concentration noise as a function of different measurement conditions according to some embodiments of the present disclosure. The spatially averaged measurements discussed with respect to FIG. 7 may be used to determine an average of gas concentration noise for different measurement regions (e.g., different measurement pixels). A measurement region may, for example, represent a component, a piece of equipment, a site, a right-of-way, or any general geographic area. The gas concentration noise may be influenced by various measurement factors, such as the altitude at which the measurements were collected, the equipment used to take the measurements, and so forth.

The pixel concentration noise values may be used to determine an average concentration noise for a region within a lidar scan area (e.g. multiple pixels). For example, the average concentration noise near the controlled release location 801 and 803 may be determined for each scan of the emission rate detection sensitivity test. Or the average concentration noise for a site or a piece of equipment could be determined. FIG. 8 shows example sets of per-scan-averaged concentration noise measurements (circles) and test-averaged concentration noise estimates (squares) for emission rate detection sensitivity tests performed at two different flight altitudes. The average concentration noise for all flight passes performed with roughly the same measurement conditions (flight speed, flight altitude, terrain reflectivity) may be averaged to determine a gas concentration noise 802 and 804. The test averaged gas concentration noise 802 and 804 may be regarded as the gas concentration noise corresponding to the emission rate detection sensitivity function derived for that specific test. The test averaged concentration noise may then be used to scale the associated emission rate detection sensitivity function to estimate the emission rate detection sensitivity for lidar measurements performed under different measurement conditions. For example, if lidar measurements were acquired over a given facility and the 2-meter gridded concentration noise was $n_{30}$=30 ppm–m then an estimate for the detection sensitivity function associated with measurements at that facility ($\phi_{30}$ $_{ppm\text{-}m}$) may be determined using equation 10, $$\phi_{30ppm-m} = \frac{n_{30}}{n_{24.5}} \phi_{24.5ppm-m}, \quad \text{Eqn. 10}$$

where $\phi_{24.5\ ppm\text{-}m}$ is the detection sensitivity function derived from the emission rate detection sensitivity test, and $n_{24.5}$ is the corresponding test averaged concentration noise 702. Other scaling factors or functional forms may alternatively/additionally be used. This method of scaling the emission rate detection sensitivity function may be validated using emission rate detection sensitivity test results performed under different gas concentration noise conditions. For example, a test performed at a different flight altitude may result in different gas concentration noise measurements, as shown in FIG. 8, where 803 are the concentration noise from each flyover pass, and 804 is the test averaged gas concentration noise. An emission rate detection sensitivity function may be derived for that set of controlled release test data using the formalism presented herein. A consistency check may then be applied to ensure the emission rate detection sensitivity function for either test can be used to derive the emission rate detection sensitivity function for the other test using equation 10. More generally, a PoD function may be generated based on gas concentration noise as a variable parameter instead of gas flow speed. For instance, a plot similar to, or analogous to, FIG. 3 may be generated, but with gas concentration noise on the horizontal axis and the data may be normalized for wind speed. And similarly, a resulting emission rate sensitivity function may be generated, this time as a function of gas concentration noise instead of gas flow speed. Ultimately, one or more PoD functions may be generated for different intervals of gas concentration noise, analogously to how PoD functions were generated for different gas flow speed intervals.

Further refinement of the detection sensitivity functions may be achieved by considering the detection sensitivity as a continuous function of both gas flow speed and gas concentration noise, $\phi(v, n)$, rather than a discrete set of functions $\phi_n(v)$ at different concentration noise values. One method for implementing this approach may be to use the measured gas concentration noise for each flyover pass to determine normalized emission rates based on the average concentration noise and the average wind speed for the set of measurement being fit with a PoD function. The normalized emission rates for a set of measurements with average wind speed $v_{avg}$ and concentration noise $n_{avg}$ may take the form, $$\varepsilon_{norm} = \varepsilon_m - \frac{\partial \phi(v, n)}{\partial v}\bigg|_{v=v_{avg}} (v_m - v_{avg}) - \frac{\partial \phi(v, n)}{\partial n}\bigg|_{n=n_{avg}} (n_m - n_{avg}) \quad \text{Eqn. 11}$$

Here, the emission rate variables and gas flow speed variables are similar to equation 6, $n_m$ is the measured concentration noise associated with each controlled release scan, $n_{avg}$ is the average concentration noise of the controlled release data set being analyzed with the regression, and $$\frac{\partial \phi(v, n)}{\partial n}\bigg|_{n=n_{avg}}$$

is the slope of the sensitivity function along the concentration noise axis evaluated at the average concentration noise for the data set being analyzed.

FIG. 9 is a graph of different PoD functions plotted for different intervals of gas concentration noises according to some embodiments of the present disclosure. The graph 900 represents one method of generating a PoD function with respect to emission rate which varies with respect to gas concentration noise. For example, the different gas concentration noise intervals may represent different measurement conditions (e.g., different measurement altitudes or different ground surface reflectivities) of the lidar system 200. As with the generation of PoD functions for different flow speeds, any method may be used to generate PoD functions for different gas concentration noises.

FIG. 9 shows example PoD functions (901 and 902) for different gas concentration noise intervals corresponding to a single wind speed interval (or normalized wind speed interval). The gas concentrations may be found as discussed above with respect to FIG. 8. Using this method PoD functions may be computed for concentration noise intervals and gas flow speed intervals that span the range of concentration noise and wind speed conditions observed during the controlled release test. Emission rate values corresponding to a specific PoD may then be extracted from the PoD functions, which themselves correspond to specific values of concentration noise and gas flow speed. The emission rate values (e.g. for one or more fixed PoDs), and corresponding concentration noise and gas flow speed values, may then be inputted into a fitting routine to create detection sensitivity function surfaces that define the emission rate for a specific PoD across the entire range of gas concentration noise and gas flow speed.

Figure 10:
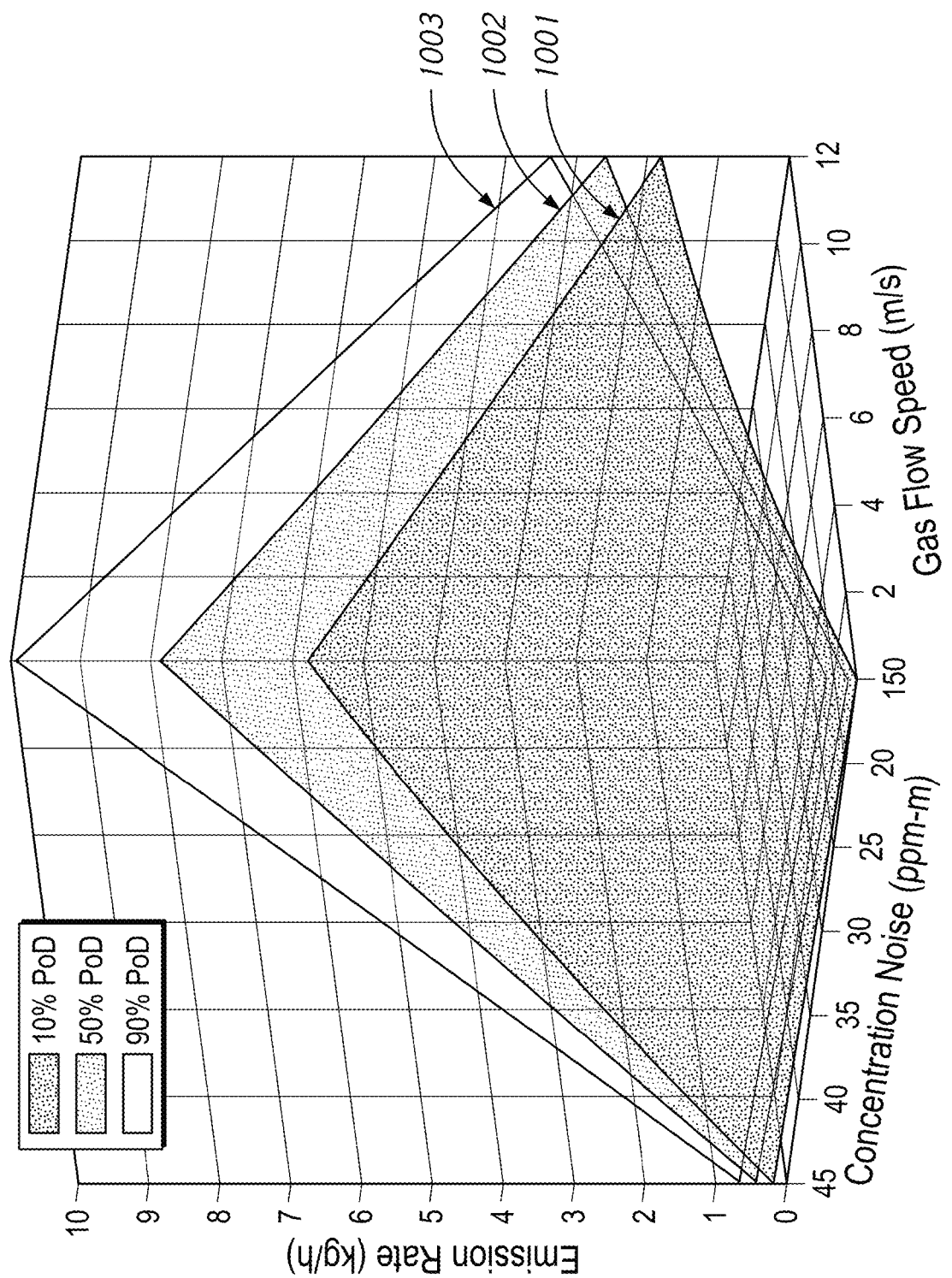
FIG. 10 is a generalized PoD function according to some embodiments of the present disclosure.

FIG. 10 is a generalized PoD function according to some embodiments of the present disclosure. The graph 1000 represents a generalized PoD function that may capture the PoD dependences on both gas concentration noise and gas flow speed, with example iso-PoD surfaces 1001-1003 generated from the generalized PoD function shown on the graph 1000. FIG. 10 shows an example of iso-PoD surfaces based on the detection data in FIG. 3 and the concentration noise data in FIG. 8. FIG. 10 shows 3 surfaces 1001, 1002, and 1003 that represent the emission rates corresponding to 10%, 50%, and 90% PoD, respectively. However, similar surfaces may be generated for any arbitrary PoD (e.g., 25%, 30%, 40%, 60%, 70%, 80% etc).

A generalized PoD function like the one represented by the graph 1000 based on one or more PoD functions such as the ones discussed in the examples of FIGS. 3-9. The generalized PoD function may be an extension that maps a multi-dimensional space (e.g., gas flow speed, gas concentration noise, emission rate and probability of detection) based on the PoD functions which represent 'slices' of that multi-dimensional space where one or more of those variables is controlled or kept relatively constant. In some embodiments, multiple PoD functions may be used to 'map' the space of the generalized PoD function, and the generalized PoD function may be fit to a set of different PoD functions where one variable is kept within a fixed interval and a set of different PoD functions is generated for different intervals of the other variable. For example, the generalized PoD function may be generated by determining a set of PoD functions each for a different gas concentration noise interval, but for a fixed gas flow speed interval (e.g. from PoD functions based on controlled releases) such as the PoD functions of graph 900 of FIG. 9. This process may be repeated for different gas flow speed intervals until the space is mapped out. In some example embodiments, the set of PoD functions may use a fixed gas concentration noise interval and different gas flow speed intervals. It may be necessary or even advantageous to use functional forms based on knowledge of the sensor measurement properties, plume fluid dynamics, and measurement conditions (e.g. a physical model), between intervals in either or both gas concentration noise and/or gas flow speed dimensions. For example, power law models for the sensitivity function along the gas flow speed and gas concentration noise axes may yield a generalized PoD function that accurately represents controlled release test data. Assumed functional forms may also be used or assumed based on extrapolation of one or more PoDs corresponding to a value or interval of gas concentration noise and gas flow speed. The PoDs are generated from emission events with controlled or otherwise known emission rates as described with respect to FIGS. 3-9

In some example embodiments, rather than fitting or otherwise generating the generalized PoD function from a set of PoD functions, a single PoD function may be used. For example, the memory (e.g. 254 of FIG. 2) may include a model which describes the relationship between the gas concentration noise, the gas flow speed, and the emission rate probability of detection. Since this model may define a general shape of the generalized PoD function, the model may be used to fit the generalized PoD function to a single PoD function. For example, a multivariate regression may be used. In some embodiments, it may not be necessary to generate a PoD function, and the generalized PoD function may be assumed based on knowledge, or a model, of the sensor and measurements behavior (e.g. a physical model). In this case, it may be desirable to validate the generalized PoD function based on one or more PoD functions (e.g. based on measurements of emissions from known emission sources).

The surfaces 1001-1003 of FIG. 10 represent a more generalized view of certain values of a generalized PoD function. For example, the surfaces 1001-1003 may be used as part of a generalized PoD function to characterize a measurement system based on multiple inputs (e.g., box 234 of FIG. 2). For example, a specified gas flow speed and concentration noise may be input to find an emission rate corresponding to a given PoD (one of the surfaces shown). An important value of the information represented in FIG. 10 may be that a PoD may be determined for a given emission rate (or an emission rate may be determined for a given PoD) under any environmental and/or operational conditions by simply determining two parameters: the gas concentration noise and the gas flow speed. The gas concentration noise may be separated, or broken out, into multiple constituent parameters (e.g. ground reflectivity, flight altitude, flight speed, etc.) to expand the dimensionality of the space, at the expense of added complexity. The information shown in FIG. 10 may provide a simple means of assessing an emission rate detection sensitivity performance of an instrument under multiple unknown or inaccurately known environmental or operational conditions that may represent constituent parameters of the gas concentration noise.

In some embodiments, various parameters which are derived from, or used to find, the gas concentration noise and/or gas flow speed may be used instead of those two parameters. For example, a parameter such as wind speed, which may act as a proxy for gas flow speed may be used, or a variable calculated based on the gas concentration noise. In some embodiments, multiple environmental and/or operational parameters may be represented by two independent variables (e.g. gas concentration noise and gas flow speed).

Figure 11:
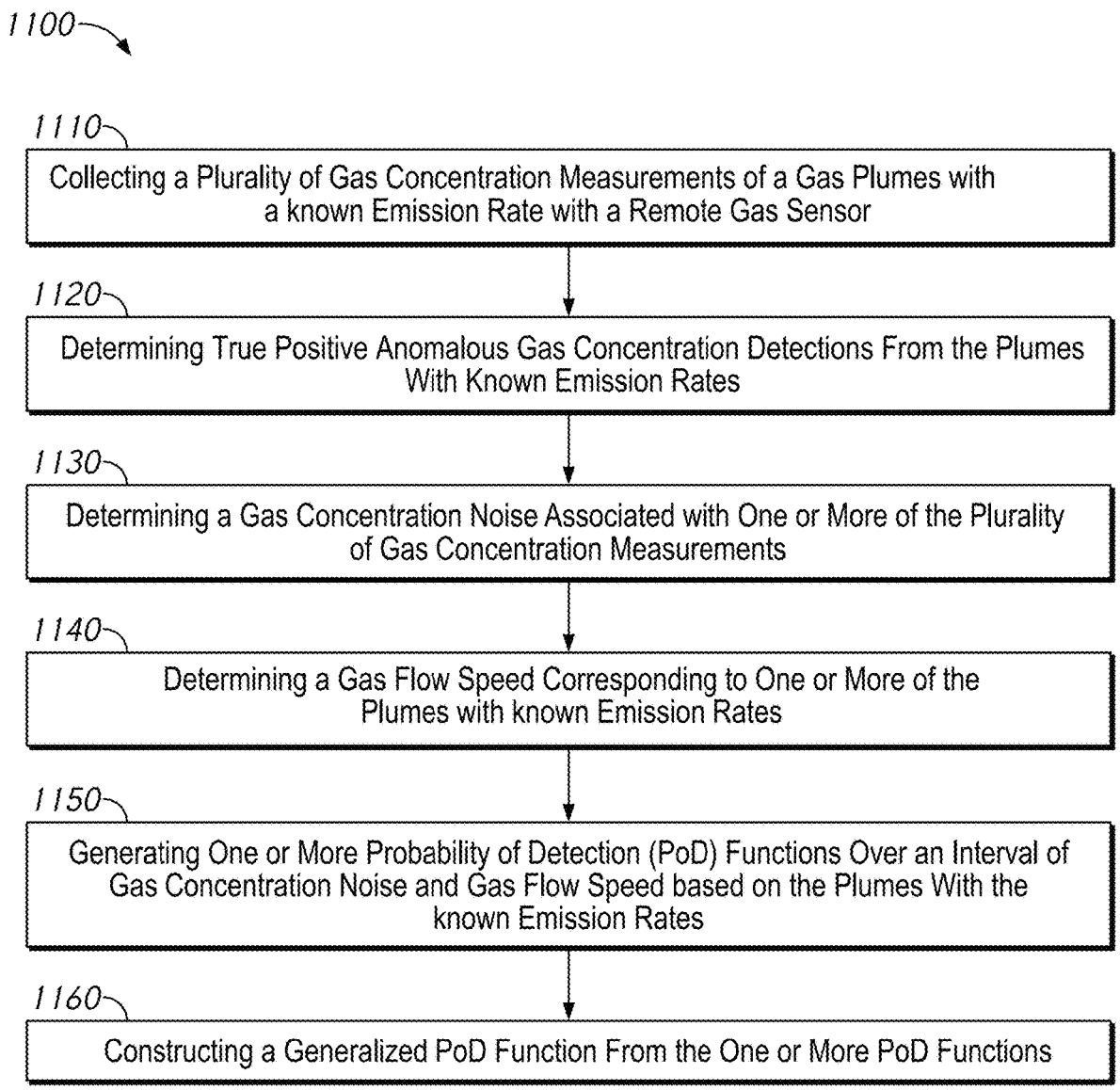
FIG. 11 is a flow chart of a method of determining a generalized probability of detection function according to some embodiments of the present disclosure.

FIG. 11 is a flow chart of a method of determining a generalized PoD function according to some embodiments of the present disclosure. The method 1100 of FIG. 11 may be implemented by one or more of the systems or apparatuses described herein. For example, the method 1100 may represent an example implementation of the steps of the box 232 of FIG. 2.

The method 1100 includes box 1110, which describes collecting a plurality of gas concentration measurements of gas plumes (or emission sources) with known emission rates with a remote gas sensor. For example, the method 1100 may include emitting gas from a metered emission source with a known flow rate (e.g. mass flow rate) and collecting one or more measurements of the emitted gas with a lidar system, such as the lidar system 110 of FIGS. 1 and/or 200 of FIG. 2. The method 1100 may include collecting the measurements over one or more measurement conditions, such as multiple emission rates, different altitudes, different etc. The steps of box 1110 may be similar to the steps of box 210 of FIG. 2 in some example embodiments.

The method 1100 includes box 1120, which describes determining true positive anomalous gas concentration detections from the plumes with known emission rates. In other words the box 1120 may describe determining which of the plurality of gas concentration measurements detected the gas plume(s). If the emission of gas is certain (e.g., because the release was controlled and therefore known to have occurred), an undetected gas plume may be referred to as a false negative and a detected gas plume may be referred to as a true positive. In some embodiments, the box 1120 may include determining both false negatives as well as true positives of the anomalous gas concentration detections. The method 1100 may include applying a threshold to the measurements to determine if they are sufficiently above a background level. In some example embodiments, information about the spatial distribution of the plurality of measurements may be used. For example, the method 1100 may include checking different contiguous regions based on the spatial grouping of the measurements to determine if a plume is detected or not.

The method 1100 includes box 1130, which describes determining a gas concentration noise associated with one or more of the plurality of gas concentration measurements. For example, the gas concentration noise may be based on a noise model (e.g., Eqn. 1). In some embodiments, the gas concentration noise may be calculated based on one or more properties of the gas concentration measurements, such as power received by the photodetector, SNR of the measurement, or combinations thereof. In some embodiments, there may be a gas concentration noise associated with each of the gas concentration measurements. In some embodiments, the gas concentrations noise may apply to selected ones of the gas concentration measurements. In some embodiments each gas concentration noise may apply to multiple of the gas concentration measurements.

In some embodiments, the method 1100 may include spatially resampling the gas concentration measurements. For example, the method 1100 may include applying a uniform grid pattern to the measurements, such as in the example of FIG. 7. The spatially resampled data may be used in later steps of the method, such as to generate a PoD function in box 1150.

The method 1100 includes box 1140, which describes determining a gas flow speed corresponding to one or more of the known emission rates. The gas flow speed may, in some embodiments, be determined based on a wind speed. The method 1100 may include measuring a wind speed. In some embodiments, the wind speed may be determined based on data gathered from one or more databases, models, forecasting information, other source, or combinations thereof.

The method 1100 includes box 1150, which includes generating one or more probability of detection (PoD) functions over an interval of gas concentration noise and gas flow speed based on the plumes with the known emission rates. The method 1100 may include generating the PoD function(s) as a function of emission rate for one or more gas flow speed interval (e.g., FIGS. 3-6), gas concentration interval, or combinations thereof (e.g., FIG. 7-9). The intervals may represent the total interval across the entire measurement or subsets of measurements, or a single value (e.g. one gas concentration value). For example, the method may include dividing the gas concentration noise, the gas flow speed or combinations thereof into different ranges. The method 1100 may include generating the PoD function based on fitting one or more data points generated from an emission sensitivity function (e.g., FIGS. 3-4). The method 1100 may include generating the PoD function based on a logistic regression (e.g., FIG. 5).

The method 1100 may include box 1160 which describes constructing a generalized PoD function from the one or more PoD functions. For example, the method 1100 may include using the one or more PoD functions as known portions (e.g. vertical 'slices' in the graph shown) of the overall generalized PoD function and fitting parameters of the generalized PoD function to the one or more PoD functions. For example, the method 1100 may include generating a set of PoD functions within a fixed interval of one or more gas flow speed or gas concentration noise each of the set of PoD functions having a different interval of the other of gas flow speed or gas concentration noise. For example, the method 1100 may include generating a set of PoD functions such as the ones in FIG. 9 which are within a fixed gas flow speed interval but represent several different gas concentration noise intervals.

In some embodiments, box 1160 may include constructing the generalized PoD function directly from a single PoD function or from the data set (instead of from the PoD functions). The data set includes the classified (e.g., detected or not detected) gas concentration measurements as well as the gas flow rate and gas concentration noise. For example, the method 1100 may include fitting a single PoD function or the data set (e.g., with multivariate regression) using a priori knowledge, assumed function, or a model which characterizes the emission rate PoD of the measurement system as a function of gas flow speed and gas concentration noise.

In some embodiments, box 1160 may include constructing the generalized PoD function using just a priori knowledge, assumed function, or a model (e.g. a physical model) which characterizes the emission rate PoD of the measurement system as a function of gas flow speed and gas concentration noise, instead of a PoD function. In this case, it may be desirable to validate, or assess the error of, the model using one or more PoD functions based on measured emissions with known emission rates.

The method 1100 may include characterizing a performance of the measurement system based on the generalized PoD function (e.g., box 234 of FIG. 2). In some embodiments, the method 1100 may include estimating missed detections (e.g., box 236 of FIG. 2). For example, the method 1100 may include collecting a plurality of field gas concentration measurements corresponding to emission sources for which the emission rates are not known, determining emission rates based on the field plurality of gas concentration measurements, and using the generalized PoD function to estimate a number or an amount (e.g. total emission rate) of missed emission sources (e.g. false negative detections) based on the emission rates. For example, in a simplified scenario, where all emissions were detected in the same environmental conditions, the number of total emission sources (e.g. detected plus missed) at the emission rate may be determined by dividing the number of detected emission sources at the emission rate by a probability of detection at that emission rate determined from the generalized PoD function. In general scenarios, resampling of the detected emissions based on the PoD for each detection and the environmental conditions which they were measured may be required to estimate the number and total rate of missed emission sources. In some embodiments, the method 1100 may include generating improved emission rate estimates (e.g., box 238 of FIG. 2).

FIGS. 12-14 describe an example application for the generalized PoD function. The example of FIGS. 12-14 describe using the generalized PoD function to estimate missed detections (e.g., box 236 of FIG. 2). FIG. 12 shows an example measured cumulative distribution, and FIG. 13 shows an example estimated cumulative distribution which includes the estimated missed detections.

FIG. 12 is a graph of an example cumulative emission rate distribution curve of detected and quantified emission rates according to some embodiments of the present disclosure. The graph 1200 shows a plot 1201 of the aggregated fraction of the total measured emission rate as a function of the emission rate for each measured emission event. In this example, the cumulative emission rate distribution curve 1201 is determined from a set of detected and quantified emissions, each having an associated emission rate. As previously described, the lidar system (e.g., 110 of FIG. 1) may gather gas concentration measurements, which may be combined with gas flow speed information (e.g., wind speed) to generate measured emission rates. For example, the measurements may be gathered from a site by a mobile platform (e.g., 101 of FIG. 1) flying over a target area one or more times. The computed total fractional emissions for a set of measured emissions may then be plotted against the emission rate to produce curve 1201. However, emission events corresponding to, for example, emission rates below the emission rate detection sensitivity, may not be detected, and may therefore may not be included in the cumulative emission rate distribution of FIG. 12.

The measured emission rates may be used to generate a cumulative curve 1201 by first sorting the detected emissions by emission rate in descending order, and then performing a cumulative sum, and then dividing the cumulative sum by the sum of all emission rates in the set to create a normalized distribution. For example, FIG. 12 shows an example cumulative emissions distribution data set containing more than 11,000 detected emissions acquired from a lidar gas mapping survey of tens of thousands of oil and gas production sites. In this example, the cumulative emissions distribution curve 1201 is computed by sorting the emission rate estimates for all detections in the data set in descending order and then performing a cumulative sum on the set and then dividing by the sum of all measured emission rates in the set.

The data in FIG. 12 represent gas emissions which were successfully detected by the lidar system. However, some gas plumes will have been missed because, for example, the PoD for that emission rate was less than 100% for the gas concentration noise and gas flow speed conditions of the measurement (see FIG. 10). Nevertheless, the probability that a gas plume is detected may be estimated based on the generalized PoD space as a function of emission rate, taking into account the measurement conditions in which each gas plume was measured (e.g., as shown in FIGS. 4-7 or FIG. 10, for example). PoD estimates may be applied to the detection events for each detection in 1201 to estimate the fraction of emissions that were not detected by the lidar sensor, but in fact may have been (from a statistical standpoint) occurring during the scan.

FIG. 13 is a graph of an example estimated total fractional emission rate curve according to some embodiments of the present disclosure. The graph 1300 of FIG. 13 shows how the data set represented in the graph 1201 of FIG. 12 may be updated based on a generalized PoD function associated with the measurement conditions under which the data of the curve 1201 were collected. For example, the PoD curve may be generated as a function of emission rate in a manner similar to discussed above with respect to FIGS. 3-11 and/or box 232 of FIG. 2.

Example estimated total emission rate 1301 and measured total emission rate 1302 cumulative distribution curves are shown in the graph 1300. The estimated total emission rate curve 1301 is generated from the measured total emission rate curve 1201 after application of the PoD to each measured emission 1201 to estimate the number of emission events, and associated amount of emissions, that may have been (from a statistical standpoint) occurring but not detected by the sensor during the survey as well as the emissions that were detected. The measured emission rate curve 1302 represents an adjusted set of measurements which show how many measurements were detected compared to the estimated distribution of emission rates 1301. The Estimated Total Emission Rate curve 1301 represents cumulative distribution of detected emissions plus estimated missed emissions. The measured curve 1301 represents the cumulative distribution of detected emission rates divided by the sum of detected emissions plus missed emissions.

For example, Curve 1301 provides estimates for the total emission rate detected by the sensor during the scan, plus emissions not detected by the sensor based on the PoD functions and the distributions of gas flow speed and gas concentration noise associated with the scan measurements in the emission rate range between 20 scfh and 100,000 scfh. The estimated emission rate curve 1301 may be computed by dividing the cumulative emissions distribution curve 1201 by the sum of the estimated total emissions curve 1301. In this example, the lidar sensor is estimated to have detected 96% of emissions between 20 scfh and 100,000 scfh during the survey. Each site or piece of equipment scanned may have a different PoD function depending on the gas concentration noise or gas flow speed at for that site at the time of measurement. The average gas concentration noise and gas flow speed for a given interval of detected emission rates may be determined. Using this information, the number of detection events within that emission rate interval may be scaled to estimate the determined the number of emission events that were not detected, according to, for example the PoD at that emission rate interval, the average gas concentration noise, and average gas flow speed. For example, if N emission sources with a given emission rate were detected and the PoD at that emission rate was p, then it may be estimated that there were actually N/p emission sources present during the scan and N(1−p)/p of the emission sources were not detected. This is only one example. There are multiple possible ways to scale the detection events by a PoD (generalized or otherwise) to estimate a number of undetected emission events or emissions.

FIG. 14 is a flow chart of a method according to some embodiments of the present disclosure. The method 1400 may be implemented by any of the apparatuses or systems described herein. The method 1400 may be implemented by the lidar system 110 of FIGS. 1 and/or 200 of FIG. 2 in some example embodiments. For example, the method 1400 may be implemented by instructions in the computing system 201 of FIG. 2.

The method 1400 includes block 1410 which describes determining measured emission rates of gas plumes based on flow information and gas concentration measurements collected with a measurement system. The steps of block 1410 may generally be similar to the steps of blocks 218-222 of FIG. 2 and so for the sake of brevity the details will not be repeated again. In brief, the method 1400 may include collecting gas concentration measurements, determining flow information (e.g., by determining wind speed) and finding the emission rates based on the concentration measurements and the gas flow speed.

Block 1410 may generally be followed by block 1420, which describes generating a cumulative distribution of the gas plumes based on the determined emission rates. For example, the cumulative distribution may be plotted as what percentage of the detected plumes were at or above a given emission rate (e.g., FIG. 12).

Block 1420 may generally be followed by block 1430, which describes generating an estimated cumulative distribution based on the cumulative distribution, measurement conditions during the scan, and a generalized probability of detection (PoD) function of the measurement system. For example, for each detected emission rate, the missed emissions in similar conditions may be estimated. If all plumes were measured in the same conditions the amount of missed emissions at each emission rate may be estimated by multiplying the emission rate by $(1-p)/p$, where p is the PoD for that emission rate. In a more general scenario, where each emission is detected in different conditions, the PoD may incorporated in a Monte Carlo simulation to estimate the number of emissions and associated emission rates that would be detected and missed for a given scan based on the generalized PoD function and the measurement conditions during the scan. In some embodiments, the estimated total emission rate may be plotted as a cumulative function. In some embodiments, an adjusted measured cumulative emission rate curve may be determined for example by showing the measured emission rate as a percentage of the estimated total emission rate. In some embodiments, the cumulative distribution, the estimated distribution, the adjusted cumulative distribution or combinations thereof may be displayed to a user (e.g., via display 202). For example, as in the graph 1300 of FIG. 13 which displays the estimated cumulative distribution and the adjusted cumulative distribution.

The method 1400 may also include determining a probability of detection (PoD) as a function of emission rate (e.g., as in the method 1100 of FIG. 11). For example, the PoD may be generated in a manner similar to described in FIGS. 3-11. The PoD may be generated based on similar measurement conditions as were used to collect the measurements (e.g., similar gas flow speed, similar flight altitude, etc.).

FIGS. 15-16 show an example application for using the generalized PoD function to generate improved emission rate estimates (e.g., box 238 of FIG. 2).

FIG. 15 is a flow chart of a method for comparing the emission rate detection PoD and the gas concentration detection PoD to compute an improved emission rate estimate according to some embodiments of the present disclosure.

An emission rate may be calculated from remote sensing gas concentration imagery by combining gas concentration measurements with one or more gas flow speed estimate(s) in a computation that produces an emission rate estimate. Gas flow speed estimates may be derived from several information sources including but not limited to in-situ anemometer data, local weather station data, remote weather model data, and/or inferred from a gas plume divergence determined from gas concentration imagery. Uncertainty in the gas flow speed may represent a large portion of uncertainty in an emission rate estimate due to lack of information about the wind speed near a detected gas plume. FIG. 15 shows a block diagram of a method for producing an additional estimate of the gas flow speed by comparing the emission rate PoD and the gas concentration PoD for a given detection.

The method 1500 includes block 1510 which describes detecting a gas plume based on a gas concentration measurement. This may be generally similar to block 1410 or blocks 218-222 of FIG. 2 and so for the sake of brevity the details will not be repeated.

Block 1510 may be followed by blocks 1520 and block 1540. Block 1520 describes determining a first PoD value based on the gas concentration measurement. For example, block 1520 may include determining the plume signal to noise ratio (SNRm) and computing the gas concentration PoD ($PoD_{GC}$). The $PoD_{GC}$ may be determined as a function of the SNR, as described in more detail below with respect to Eqn. 13.

Block 1540 describes combining gas flow speed data (e.g., wind speed) with plume concentration measurements (e.g., collected by a lidar system) to determine an initial gas emission rate estimate. Block 1540 may generally be followed by block 1550 which describes determining a second PoD value based on the gas emission rate estimate using gas flow speed data, gas concentration noise data, and a generalized PoD function (e.g., as discussed in FIGS. 3-11). For example, the block 1550 may include determining a emission rate PoD ($PoD_{ER}$) by plugging in the gas concentration noise and gas flow speed information into the generalized PoD function.

Boxes 1520 and 1550 may be followed by boxes 1530 and 1560 which together describe finding an adjusted emission rate of the gas plume based on the initial emission rate, the first PoD value and the second PoD value. For example, box 1530 describes determining an emission rate such that $PoD_{ER}$ matches $PoD_{GC}$. If the two PoD's do not match, it may be due to a faulty determination of the gas flow speed since the gas flow speed may generally be determined with less reliability than the gas concentration. Under ideal circumstances, the two PoDs should match. If they do not, since $PoD_{ER}$ depends on gas flow speed (e.g., as part of the emission rate) and $PoD_{GC}$ does not, the difference may be attributable to the gas flow speed determination.

Boxes 1530 and 1550 may be followed by box 1560, which describes computing a refined emission rate estimate using weighted average of initial emission rate estimate and PoD emission rate estimate. The steps of box 1560 (as well as other steps of the method 1500) may be described with respect to FIG. 16.

FIG. 16 is a graph which shows an example method for adjusting a gas flow speed estimate based on a comparison of the emission rate PoD and the gas concentration PoD according to some embodiments of the present disclosure. In this example, the initial emission rate estimate 1601 has an emission rate $PoD_{ER}$ corresponding to 8σ of a normal distribution (or 8 standard deviations) above the 50% PoD emission rate. For the same detection the gas concentration $PoD_{GC}$ is only 3σ above gas concentration detection threshold. In this case, the gas flow speed value that is used to compute the emission rate may be adjusted from 3 m/s to 0.9 m/s such that both the emission rate $PoD_{ER}$ and the gas concentration $PoD_{GC}$ are 3σ. As the gas flow speed is adjusted the emission rate estimate changes along the line connecting the initial emission rate estimate and the origin, since in the limit of zero gas flow speed the emission rate estimate goes to zero. By adjusting the gas flow speed from 3 m/s to 0.9 m/s the emission rate estimate is reduced from 3.5 kg/h to 1 kg/h.

An example of this method is shown in FIG. 16. In this example, normal Gaussian statistics are assumed, but other statistical behavior may be handled in analogous ways. Here, the initial gas flow speed estimate resulted in an emission rate estimate 1601 of 3.5 kg/h with an emission rate PoD of 8-sigma above the 50% PoD emission rate. The gas concentration and associated noise value for each lidar measurement, gas concentration image pixel, or larger region within the gas concentration image may be combined to compute a signal-to-noise-ratio ($SNR_m$) according to, $$SNR_m = \frac{c_m}{n_m},\qquad \text{Eqn. 12}$$

where $c_m$ is the gas concentration and $n_m$ is the noise associated with measurement m. A gas concentration probability of detection ($PoD_{gc}$) may then be computed using the following equation $$PoD_{gc} = \frac{1}{2}\left(1 + \text{erf}\left(\frac{1}{\sqrt{2}}[SNR_m - SNR_{thresh}]\right)\right) \qquad \text{Eqn. 13}$$

where $SNR_{thresh}$ is the gas concentration signal-to-noise-ratio threshold required for a region of elevated gas concentration to be flagged as a detection. For the example in FIG. 16, analysis of the region subtended by the gas plume yielded a gas concentration PoD of 3-sigma above $SNR_{thresh}$. A gas concentration PoD may have lower uncertainty than an emission rate PoD because it does not depend on a gas flow speed estimate. This may be especially true in cases where local wind speed measurements are not available, or the plume was detected in an area with complex topography that strongly affects the local wind flow. For these cases, or other cases, an improved gas flow speed estimate may be derived by computing the emission rate where the gas concentration PoD is equal to the emission rate PoD, $$PoD_{er} = PoD_{gc} \qquad \text{Eqn. 14}$$

In FIG. 16, this condition is satisfied at point 1602 where the emission rate estimate line intersects the 3σ emission rate PoD line. The resulting adjusted emission rate estimate is 1.0 kg/h corresponding to a gas flow speed of 0.9 m/s. The gas flow speed estimate produced by the PoD method may be just one of several sources of gas flow speed information. A composite gas flow speed estimate used for emission rate estimation may be computed using a weighted average of the available gas flow speed data sources. When determining a weighting function for combining the PoD gas flow speed estimate it may be useful to consider the relative difference between the slopes of the emission rate estimate line (1603) and the initial and adjusted $PoD_{er}$ lines (1604 and 1605). When these lines are close to parallel the PoD method for determining gas flow speed may be less reliable, whereas the method may be more reliable when lines 1603 and 1604/1605 are less parallel. A suitable weighting function for combing gas flow speeds using the PoD comparison method should properly account for the decreasing reliability of the PoD gas flow speed estimate as the emission rate estimate line becomes more parallel with the $PoD_{er}$ lines. The PoD method of gas flow speed estimation may be particularly useful for improving emission rate estimates for small emissions that are near the detection sensitivity limit of the remote gas concentration sensor, and for detections that are measured in low wind speed environments.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method comprising:
    collecting a plurality of gas concentration measurements of gas plumes with known emission rates with a remote gas sensor;
    determining anomalous gas concentration detections from the plumes with known emission rates;
    determining a gas concentration noise associated with one or more of the plurality of gas concentration measurements;
    determining a gas flow speed corresponding to one or more of the plumes with known emission rates;
    generating one or more probability of detection (PoD) functions each of which gives a probability the remote gas sensor will detect a gas plume over an interval of gas concentration noise and gas flow speed based on the plumes with the known emission rates; and
    constructing a generalized PoD function associated with the measurement system using the one or more PoD functions, wherein the generalized PoD function gives a probability that the remote gas sensor will detect a gas plume corresponding to an emission rate as a function of gas flow speed and gas concentration noise.

2. The method of claim 1, further comprising determining the one or more PoD functions based on a sensitivity function.

3. The method of claim 1, further comprising spatially resampling the gas concentration measurements and using the spatially resampled gas concentration measurements to generate the one or more PoD functions.

4. The method of claim 3, wherein, the spatial resampling is to a uniform grid pattern.

5. The method of claim 1, further comprising constructing the generalized PoD function based on a model that characterizes the probability that the remote gas sensor will detect a gas plume corresponding to an emission rate as a function of gas flow speed and gas concentration noise.

6. The method of claim 1, further comprising generating the one or more PoD functions based on fitting data points from a gas sensitivity function or a logistic regression of the gas concentration measurements.

7. The method of claim 1, further comprising:
    collecting a plurality of field gas concentration measurements corresponding to emissions with unknown emission rates;
    determining emission rates based on the plurality of field gas concentration measurements; and
    using the generalized PoD function and environmental conditions corresponding to the measurement collection to estimate a number and associated rates of predicted emission sources which were not detected by the plurality of field gas concentration measurements based on emission rates determined from detected emissions.

8. The method of claim 1, further comprising determining the gas concentration noise based on a noise model.

9. The method of claim 1, further comprising collecting the plurality of gas concentration measurements with a lidar system.

10. The method of claim 1, further comprising characterizing a detection sensitivity performance of the measurement system based on the generalized PoD function.

11. A system comprising:
a remote sensor configured to collect sensor measurements of a scene;
a processor and
a memory, the memory containing non-transitory instructions which, when executed by the processor cause the processor to:
determine a gas concentration measurement based on the measurement collected by the remote sensor and a gas concentration noise level associated with the gas concentration measurement;
determine a gas flow speed associated with the scene;
determine an emission rate based on the gas concentration measurement and gas flow speed information;
combine a generalized probability of detection (PoD) function associated with the remote sensor with the gas flow speed and the gas concentration noise to determine a detection sensitivity performance, wherein the generalized PoD function gives a probability that the remote gas sensor will detect a gas plume in the scene corresponding to an emission rate as a function of gas flow speed and gas concentration noise.

12. The system of claim 11, wherein the remote sensor is mounted on a mobile platform.

13. The system of claim 11, wherein the remote sensor includes a beam scanner configured to scan a laser across an environment.

14. The system of claim 13, wherein the remote sensor includes a receiver configured to record the measurements based on light received as the laser is scanned across the environment.

15. The system of claim 11, wherein the non-transitory instructions when executed by the processor further cause the computing system to determine a detection sensitivity performance based on the generalized PoD function.

16. The system of claim 15, wherein the non-transitory instructions when executed by the processor further causes the computing system to adjust the emission rate based, in part, on the generalized PoD function and a second PoD based on the gas concentration noise.

17. A method comprising:
determining measured emission rates of gas plumes based on gas flow speed information and gas concentration measurements collected with a measurement system;
generating a cumulative distribution of the gas plumes based on the determined emission rates; and
determining a number of emission sources or amount of emissions attributed to predicted emissions which were not detected based on a generalized probability of detection (PoD) function of the measurement system which gives a probability that the measurement system will detect a gas plume corresponding to an emission rate as a function of gas flow speed and gas concentration noise.

18. The method of claim 17, further comprising generating the generalized PoD function based on measurements of a known emission source with the measurement system.

19. The method of claim 17, further comprising generating an adjusted cumulative distribution relative to the estimated cumulative distribution.

20. The method of claim 17, further comprising displaying the cumulative distribution, the estimated distribution, the adjusted cumulative distribution or combinations thereof.

21. A method comprising:
detecting a gas plume based on a gas concentration measurement with a measurement system;
determining a first probability of detection (PoD) value based on the gas concentration measurement;
combining the gas concentration measurement with a gas flow speed to determine an initial emission rate of the gas plume;
determining a second PoD value based on the gas concentration measurement and the gas flow speed and a generalized PoD function wherein the generalized PoD function gives a probability that the measurement system will detect a gas plume corresponding to an emission rate as a function of gas flow speed and gas concentration noise; and
finding an adjusted emission rate of the gas plume based on the initial emission rate, the first PoD value and the second PoD value.

22. The method of claim 21, further comprising finding the adjusted emission rate based on finding an estimated emission rate where the first PoD value matches the second PoD value.

23. The method of claim 22, further comprising determining the adjusted emission rate based on a weighted average of the initial emission rate and the estimated emission rate.

24. The method of claim 21, further comprising determining the first probability of detection based on a gas concentration noise based on the gas concentration measurement.

25. The method of claim 21, further comprising determining the generalized PoD function based on measurements of a known emission rate.

* * * * *